US008852150B2

(12) United States Patent
Wang

(10) Patent No.: US 8,852,150 B2
(45) Date of Patent: Oct. 7, 2014

(54) DC-AC FREQUENCY CONVERTER TYPE NOSE CLEANER

(75) Inventor: Ming Yang Wang, Nantou (TW)

(73) Assignee: Jackey Chiou, Nantou (TW)

( * ) Notice: Subject to any disclaimer, the term of this patent is extended or adjusted under 35 U.S.C. 154(b) by 567 days.

(21) Appl. No.: 12/871,929

(22) Filed: Aug. 31, 2010

(65) Prior Publication Data

US 2012/0053519 A1     Mar. 1, 2012

(51) Int. Cl.
    *A61M 37/00*     (2006.01)
    *A61M 3/02*     (2006.01)

(52) U.S. Cl.
    CPC ..... *A61M 3/0258* (2013.01); *A61M 2210/0618* (2013.01); *A61M 3/0279* (2013.01)
    USPC ............................ 604/131; 604/132; 604/151

(58) Field of Classification Search
    USPC ........ 604/24, 93.01, 118, 131, 151, 132, 133, 604/152, 540; 417/412, 413.1; 318/124, 318/123, 129, 132
    See application file for complete search history.

(56) References Cited

U.S. PATENT DOCUMENTS

| | | | | |
|---|---|---|---|---|
| 3,671,151 A | * | 6/1972 | Duke et al. | 417/411 |
| 4,792,293 A | * | 12/1988 | Wang | 417/571 |
| 5,011,379 A | * | 4/1991 | Hashimoto | 417/360 |
| 5,137,432 A | * | 8/1992 | Tsai | 417/312 |
| 5,259,728 A | * | 11/1993 | Szpunar et al. | 416/2 |
| 5,472,317 A | * | 12/1995 | Field et al. | 417/234 |
| 6,168,392 B1 | * | 1/2001 | Takano | 417/312 |
| 6,241,705 B1 | * | 6/2001 | Ko-Wen | 604/73 |
| 6,340,069 B1 | * | 1/2002 | Wang | 181/272 |
| 7,785,300 B2 | * | 8/2010 | Ishii et al. | 604/256 |
| 8,480,382 B2 | * | 7/2013 | Wang | 417/413.1 |
| 2010/0137781 A1 | * | 6/2010 | Wang | 604/24 |
| 2010/0286597 A1 | * | 11/2010 | Wang | 604/35 |

\* cited by examiner

*Primary Examiner* — Laura Bouchelle
(74) *Attorney, Agent, or Firm* — Raymond Y. Chan; David and Raymond Patent Firm

(57) ABSTRACT

A DC-AC frequency converter type nose cleaner includes an electromagnetic pump, a container storing a cleaning solution, a nose-washing tool and a frequency converter circuit driving the electromagnetic pump. The frequency converter circuit at least includes an oscillator circuit, a bistable circuit and a push-pull circuit. The swing speed, the swing frequency and the swing amplitude of the swing arms vary with the change of the oscillation frequency of the oscillator circuit. The DC-AC frequency converter type nose cleaner can change the pressure and the flow generated by the electromagnetic pump so as to satisfy the requirement of the discharge pressure and flow of the nose cleaner so as to overcome the defect of the discharge pressure of the conventional nose cleaner that is too big to hurt the user.

20 Claims, 38 Drawing Sheets

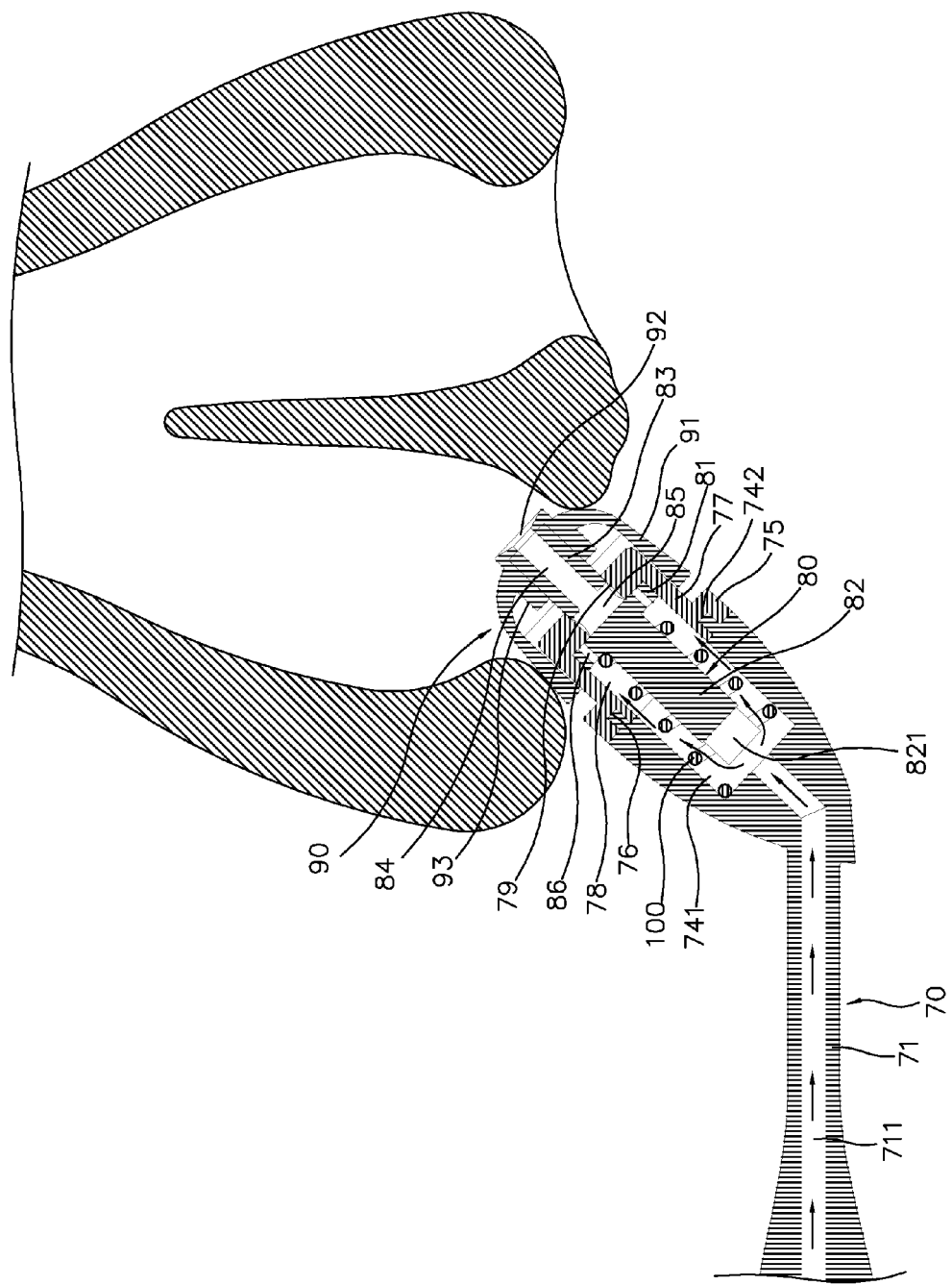

DC-AC FREQUENCY CONVERTER TYPE NOSE CLEANER

BACKGROUND OF THE PRESENT INVENTION

1. Field of Invention

The present invention relates to a DC-AC frequency converter-type nose cleaner, and more particularly to a nose cleaner with an electromagnetic pump supplied with AC power obtained from the oscillation of DC power, wherein the speed, the frequency, and the amplitude of the swing arms of the electromagnetic pump vary with the frequency of the switching between the N-phase and the S-phase of the electromagnetic device, whereby the discharge pressure and the discharge flow generated in the electromagnetic pump will satisfy the requirement of the nose cleaner.

2. Description of Related Arts

Most upper respiratory tract infections, including nasosinusitis and nasal allergies, are caused by the ataxia of the cilia on the nasal mucosa. Contaminants and bacteria drawn in through the nose can be effectively removed by the regular movement of the cilia on the nasal mucosa, thereby protecting the health of the individual.

The nasal sprayers commonly on sale on the market or in use for "ear-nose-throat" ailments treatment (ENT ailments) mainly utilize ultrasonic vibrations to atomize the liquid medicines into micro particles so that the atomized medicines can be rapidly and easily breathed into the respiratory tracts and the lungs of human bodies for a desired treatment. However, these nasal sprayers cannot substantially mend the ataxia of the cilia.

Accordingly, a conventional nose cleaner, as shown in FIG. 9, requires the user to bend their head downward, open their mouth to breath, and then a nose-washing tool is used to inject the cleaning solution or warm salt water, which is at about 35-38 degree Celsius, into the nasal cavity of one side of the nose. The cleaning solution flows through the nasopharynx and flows out from the nasal cavity through the other side of the nose, wherein this cleaning assists the movement of the cilia on the nasal mucosa. This is helpful in the prevention of colds, allergic rhinitis, nasosinusitis, halitosis, backflow of the nasal mucus, etc.

Currently, the technology of nose cleaners still focuses on the controlling the intensity of the water flow. Although high pressure water flow will provide better cleaning, it may choke the user, cause damage to the nasal mucosa, or even cause severe pain to the someone with sinuses swollen; therein leading to secondary damage. If the pressure of the water flow is too low, the effect of the cleaning will be reduced. As the proper intensity of the water flow varies from person to person, it is hard for the producers to handle.

Referring to FIGS. 1-7, an electromagnetic pump 20 is disclosed, which could also be called as a swing arm pump or a matrix type pump. The electromagnetic pump 20 is lightweight and could be operated with less noise, lower power consumption, and little chance to generate a high heat. The electronic circuit, of the electromagnetic pump, is hard to short circuit when the inlet and the outlet channels are blocked. Hence, the above mentioned electromagnetic pump is a good choice for mechanical work in medical apparatuses and instruments. The electromagnetic pump 20 has an electromagnetic device 27 on one side and a pump housing 21 on the other side. Each of two outer opposing sides of the pump housing 21 provides a stretchable and elastic bladder 24, which further provides a swing-arm 25 respectively thereon. One end of each swing arm 25 is disposed on the outer side of the pump housing 21, and a magnetic member 26 is provided on the other end of each swingarm 25 at a predetermined distance from the electromagnetic device 27. The inside of the pump housing 21 is divided into chamber 211 and chamber 212, wherein chamber 211 communicates with two inlet tubes 22, and chamber 212 communicates with two outlet tubes 23. Referring to FIGS. 2 and 3, the electromagnetic device 27 has two side magnetic members 271 and a middle magnetic member 272, wherein the polarity of the three members alternate between N-phase and S-phase. Two magnetic members 26 are respectively disposed opposite to the pair of side magnetic members 271, and have N-phase outside surfaces and S-phase inside surfaces, respectively. As shown in FIG. 2, when the two side magnetic members 271 of the electromagnetic device 27 switch to N-phase and the middle magnetic member 272 switches to S-phase; the two magnetic members 26 are attracted by the middle magnetic member 272 and are repulsed by the two side magnetic members 271 to bring the swingarms 25 towards the middle. In contrast, as shown in FIG. 3, when the two side magnetic members 271 of the electromagnetic device 27 switch to S-phase and the middle magnetic member 272 switches to N-phase; the two magnetic members 26 are repulsed by the middle magnetic member 272 and are attracted by the two side magnetic members 271 to bring the swingarms 25 towards the outside. The speed, frequency, and amplitude of the swing arm 25 is relative to the predetermined frequency of the power source, and the discharge pressure and flow.

Referring to FIGS. 4-7, when the swing arms 25 swings towards the outside to expand the bladder 24, the two first check valves 241, respectively provided between the pump housing 21 and the bladders 24, are set to open to allow a fluid flow into the first chamber 211 through the inlet tubes 22 on the outside of the pump. The fluid then flows into the two bladder 24 and then is stopped from flowing into the second chamber 212 by two second check valves 242, as the two second check valves 242 are turned off. When the two swingarm 25 swing towards the middle to compress the two bladders 24 respectively, the two second check valves 242 are turned on and the first check valves 241 are turned off; therefore, the fluid in the two bladders 24 could only flow into the second chamber 212, but reflow back into the first chamber 211. The fluid in the second chamber 212 is discharged from the pump housing 21 through the two outlet tubes 23. With the designs mentioned above, the pump housing 21 draws fluid from the inlet tubes 22 and then discharges the fluid from the outlet tube 23 to accomplish the objective of transporting the fluid. As shown in FIG. 8, the outlet tubes 23 connect to a nose-washing tool 50, wherein the nose-washing tool 50 could be used to clean the nose.

The electromagnetic pump 20 must be supplied with AC power to drive the two swing arms 25 to swing back and forth. The voltage of the domestic electricity used in the countries worldwide is either 110V or 220V. For example, the domestic electricity in Taiwan is single phase electricity with a voltage of 110V and a frequency of 60 Hz. When alternating current electricity of 110V and 60 Hz is used as the power source of the electromagnetic pump 20; the speed, frequency and amplitude of the swinging of the swing arms 25 of the electromagnetic pump 20 are fixed and cannot be adjusted. These parameters are unable to be adjusted due to a combined effect of the magnetic field strength generated in the electromagnetic device 27, the length and width of the swing arms 25, the magnetic strength of the magnetic members 26, and the elasticity of the bladders 24. That means the pressure and the flow of the discharge of the electromagnetic pump 20 cannot be adjusted according to the requirement of the pressure and/or the flow. Hence, when the electromagnetic pump 20 is applied to the nose cleaner, the discharge force might be so large to choke the user or cause damage to the nasal mucosa and the sinuses. Conversely, the discharge force may be too small to clean the nasal cavity well.

Referring to FIGS. 8 and 9, the prior art of a nose-washing tool 50 has a hollow handle 51, an extension tube 53, a connecter 52 disposed on the top end of the handle 51 for communicating with the extension tube 53, a spray nozzle 54 communicated with the extension tube 53, and a fluid inlet connecter 55 disposed on the bottom end of the handle 51 for supplying the cleaning solution or physiological saline or warm salt water; wherein the fluid inlet connecter 55 and the extension tube 53 are communicated with each other inside of the handle 51, wherein when button 56 of the handle 51 is switched, the spray nozzle 54 can be controlled to spray the cleaning solution. When using the nose cleaner, the user has to bend their head downward, open their mouth to breath, and then switch button 56 to control the spray nozzle 54 to inject the cleaning solution into the nasal cavity of one side of the nose. The cleaning solution flows through the nasopharynx and flows out from the nasal cavity through the other side of the nose, wherein the cleaning assists the movement of the cilia on the nasal mucosa. This is helpful in the prevention of colds, allergic rhinitis, nasosinusitis, halitosis, backflow of the mucus, etc.

The traditional nose-washing tool 50 has several disadvantages. For example, if the user has nasosinusitis or cannot not make an autonomous respiration, then the user will choke. For example, when the user feels that switching a button to turn off the nose-washing tool 50 is too slow, the user may draw the nose-washing tool 50 out of their nasal cavity too quickly and cause the spray nozzle 54 to uncontrollably spray cleaning solution everywhere. Hence, a nose cleaner and its accessories are required to be improved to satisfy people's requirements.

SUMMARY OF THE PRESENT INVENTION

According to the drawbacks of current nose cleans, which contain electromagnetic pumps that can only use a 110V AC power source, the present invention provides an electromagnetic pump that substantially accomplishes the following advantages and objectives.

The invention is advantageous in that it provides a nose cleaner with a frequency converter circuit which oscillates to convert DC into AC to supply power to an electromagnetic pump of the nose cleaner, wherein the frequency oscillation of the frequency converter circuit is able to be changed to adjust the discharge pressure and the discharge flow of the electromagnetic pump in order to obtain the most appropriate discharge pressure and flow of the nose cleaner.

Another advantage of the invention is to provide a nose cleaner which uses a general purpose power source, such as battery, in-car cigarette lighter, transformer rectifier unit (TRU), or any other suitable device to provide DC, and thus the nose cleaner could be widely used in any place with a suitable power source.

Another advantage of the invention is to provide a nose cleaner with a frequency converter circuit which further links to a modulation circuit, wherein when the swing arms swing outward, the modulation circuit is activated to accelerate the swing speed of the swing arms to further enlarge the discharge pressure of the electromagnetic pump, thereby the discharge pressure of the nose cleaner could be adjusted according to the user's requirement.

Another advantage of the invention is to provide a nose-washing tool having a touch sensitive switch which could immediately stop the injection of the cleaning solution after the nose-washing tool leaves the nasal cavity when the user chokes, as a result the nose-washing tool overcomes the splashing defect of the cleaning solution present in the traditional nose-washing tool.

Additional advantages and features of the invention will become apparent from the description which follows, and may be realized by means of the instrumentalities and combinations particular point out in the appended claims.

According to the present invention, the foregoing and other objects and advantages are attained by a nose cleaner comprising an electromagnetic pump, a frequency converter circuit (which oscillates to convert DC into AC), a nose-washing tool, and a container for storing a cleaning solution.

The electromagnetic pump has an electromagnetic device on one side and a pump housing on the other side, wherein at least one outside surface of the pump housing provides a stretchable and elastic bladder, which further provides a swing arm thereon. One end of the swing arm is disposed on outer side of the pump housing and a magnetic member is provided on the other end of the swing arm with a predetermined distance from the electromagnetic device. The inside of the pump housing is divided into two chambers, including a first chamber having at least one inlet connecter for communicating inside and outside and a second chamber having at least one outlet connecter for communicating inside and outside, wherein the first chamber and the second chamber are arranged up and down, or forth and back. A check valve is provided between each chamber and corresponding bladder. The swing arms reciprocate to cause the electromagnetic pump to draw fluid into the chambers from the inlet connecter and discharge the fluid from the outlet connecter. The inlet connecter of the electromagnetic pump is communicated with a container for storing cleaning solution, and the outlet connecter of the electromagnetic pump is communicated with a nose-washing tool. The electromagnetic pump could draw the cleaning solution from the container into the chambers of the electromagnetic pump through the inlet connecter and then drain the cleaning solution out from the nose-washing tool through the outlet connecter, wherein the cleaning solution drained from the nose-washing tool is used to clean the nasal cavity.

The frequency converter circuit comprises an oscillator circuit, a bi-stable circuit, and a push-pull circuit. The oscillator circuit oscillates to transform DC into a single-phase oscillating signal. The bi-stable circuit splits the single-phase oscillating signal into an N-phase stimulus signal and an S-phase stimulus signal; both of which respectively activate magnetism of two side magnetic members and a middle magnetic member of the electromagnetic device due to alternating switch between the N-phase and the S-phase. The two side magnetic members and the middle magnetic member are attracted or repulsed by the two magnetic members respectively to force the swing arms to reciprocate. The higher the oscillating frequency the oscillator circuit is adjusted, the higher the speed of switching between the N-phase and the S-phase of the electromagnetic device. The lower the oscillating frequency the oscillator circuit is adjusted, the lower the speed of switching between the N-phase and the S-phase of the electromagnetic device. The push-pull circuit amplifies and transports the N-phase stimulus signal and the S-phase stimulus signal to the electromagnetic pump to force the swing arms of the electromagnetic pump to swing effectively. The frequency converter circuit is arranged to use DC to activate the swing arms of the electromagnetic pump to reciprocate. The oscillating frequency of the oscillator circuit is adjusted to change the swing speed, the swing frequency, and the swing amplitude of the swing arms of the electromagnetic pump. This oscillating frequency further changes the discharge pressure, the discharge flow of the electromagnetic pump, and the relationship between the discharge pressure and the discharge flow. The oscillator circuit could be connected to a button or a keypad, which is arranged to adjust the oscillating frequency of the oscillator circuit.

In another embodiment of the present invention, the frequency converter circuit further comprises a modulation circuit which generates a single-phase oscillating signal. The N-phase stimulus signal and the S-phase stimulus signal generated in the bi-stable circuit are mixed with the single-phase oscillating signal to enhance the N-phase stimulus signal while balancing the S-phase stimulus signal to further enhance the magnetic field strength of the N-phase of the electromagnetic device. The enhancement of the magnetic field strength of the N-phase of the electromagnetic device causes the swing arms to swing inward with a higher speed and an increased force, and swing outward with a lower speed and a decreased force, whereby the discharge pressure and flow of the electromagnetic pump is increased. The modulation circuit is connected to a button or a keypad, which is arranged to activate or adjust the modulation circuit. The DC inputted into the frequency converter circuit could be supplied by an in-car cigarette lighter, a battery, or a transformer rectifier unit.

The nose-washing tool has a fluid inlet end with a handle disposed thereon and a fluid outlet end with a spray nozzle disposed thereon, wherein the cleaning solution flows from the end with the handle and is injected into the nasal cavity from the end of the spray nozzle. The spray nozzle is linked to a touch sensitive switch, which is enabled to move back and forth. When the spray nozzle is inserted into the nasal cavity, the spray nozzle will inject the cleaning solution. When the spray nozzle leaves the nasal cavity, the touch sensitive switch immediately moves back to the original position so that the spray nozzle can no longer inject the cleaning solution.

The container has a space for storing cleaning solution and is communicated with the inlet tube of the electromagnetic pump through a negative pressure channel. Thereby, the cleaning solution in the container could provide fluid in the electromagnetic pump.

Still further objects and advantages will become apparent from a consideration of the ensuing description and drawings. These and other objectives, features, and advantages of the present invention will become apparent from the following detailed description, the accompanying drawings, and the appended claims.

BRIEF DESCRIPTION OF THE DRAWINGS

FIG. 19A is a partial enlarged view of the nose-washing tool in close condition.

DETAILED DESCRIPTION OF THE PREFERRED EMBODIMENT

Figure 10:
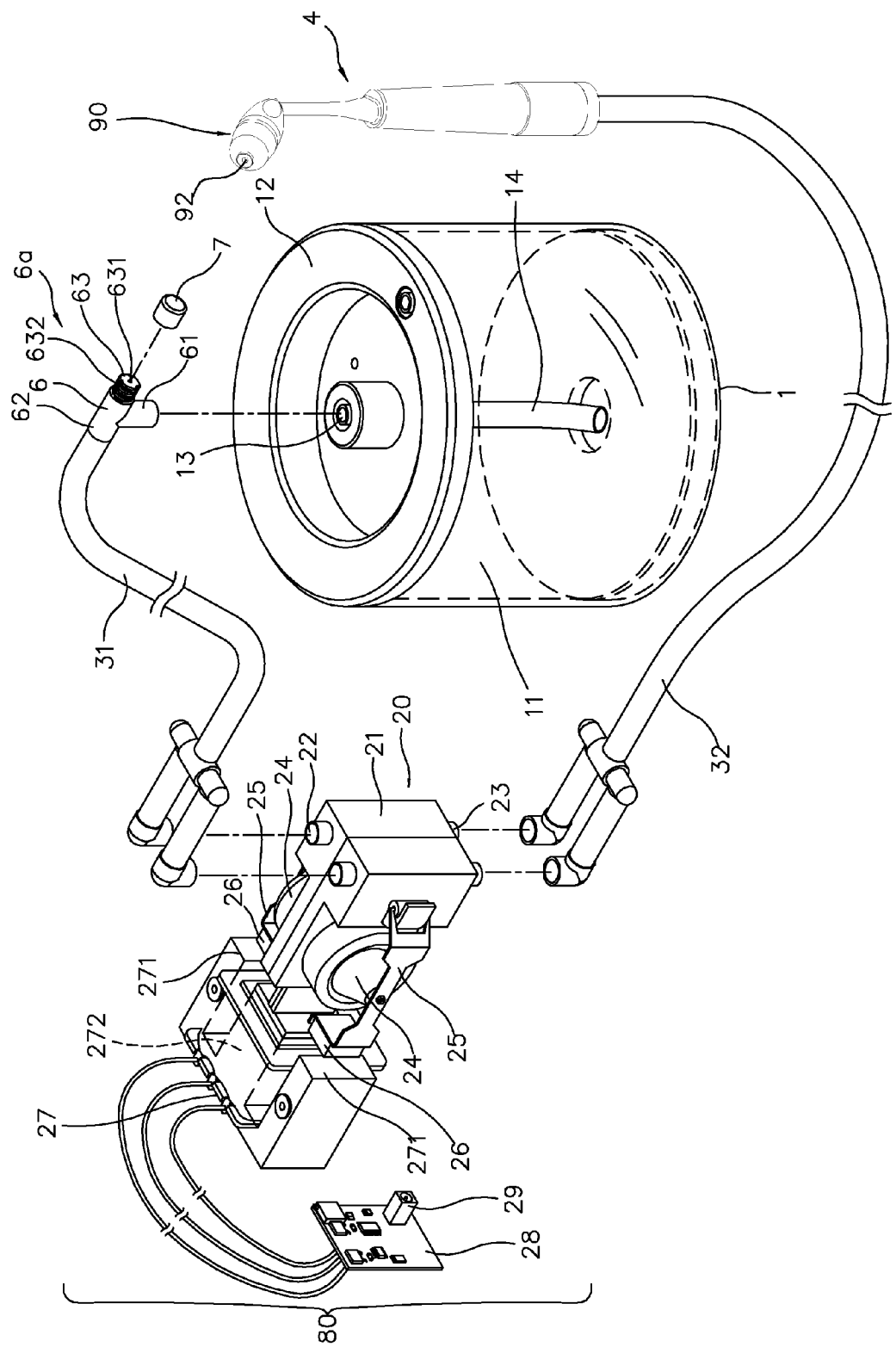
FIG. 10 is an exploded perspective view of the nose cleaner according to the above preferred embodiment of the present invention.
Figure 11:
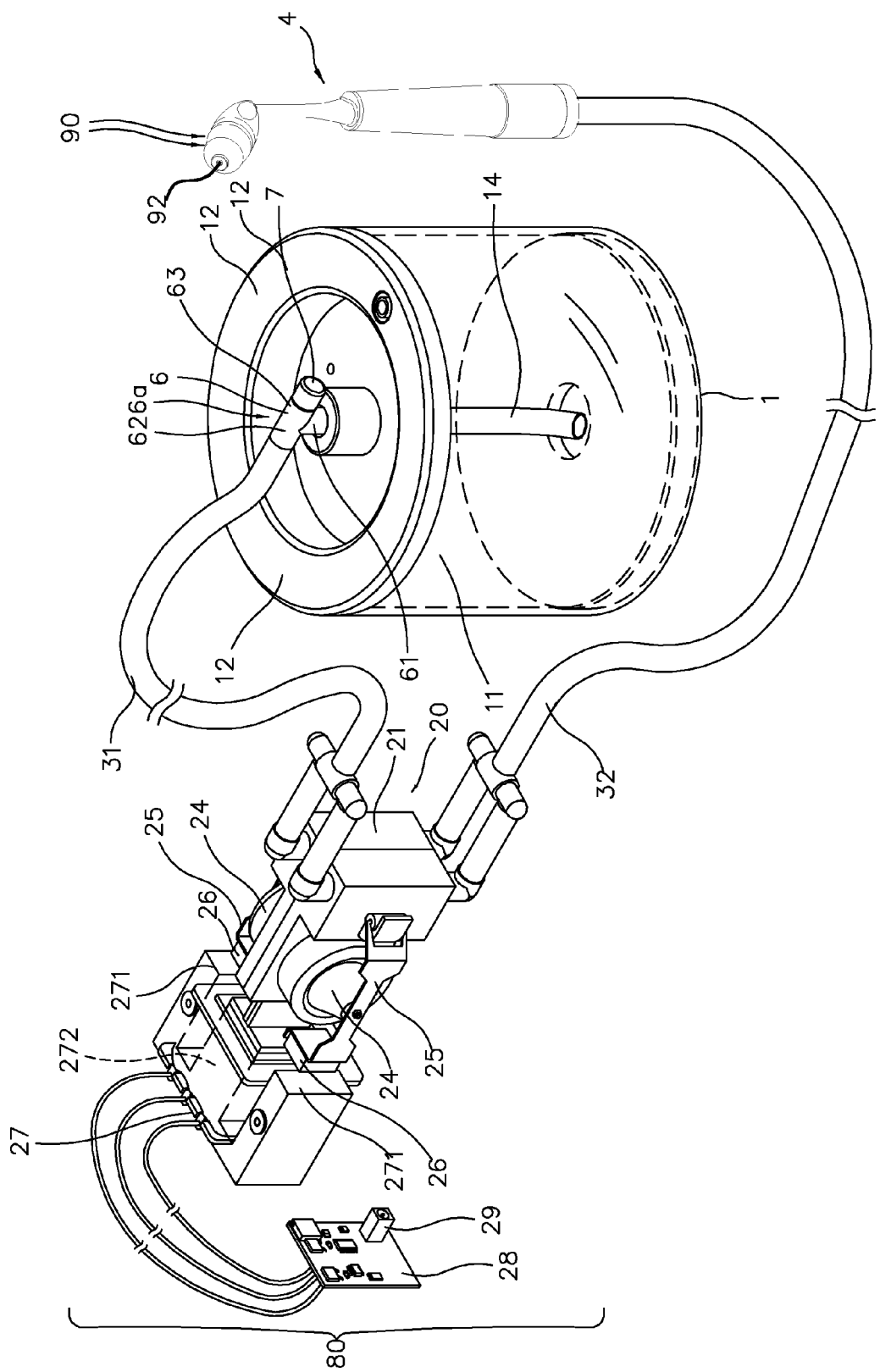
FIG. 11 is an assemble view of the nose cleaner of FIG. 10.

Referring to FIGS. 10 to 18A and 18B, a nose cleaner according to a preferred embodiment of the present invention is illustrated, which comprises an electromagnetic pump 20, a container 1 for storing a cleaning solution, a nose-washing tool 4, and a frequency converter circuit 40, wherein the frequency converter circuit 40 is provided on a circuit board 28 as shown in FIG. 10.

The electromagnetic pump 20 has an electromagnetic device 27 on one side and a pump housing 21 on the other side, wherein the electromagnetic device 27 is surrounded with coils and has a middle magnetic member 272 and two side magnetic members 271, wherein the width of the middle magnetic member 272 is larger than that of the side magnetic member 271. Each of two outside surfaces of the pump housing 21 provides a stretchable and elastic bladder 24, which further provides a swing arm 25 respectively thereon, wherein one end of each swing arm 25 is disposed on the outer side of the pump housing 21 and a magnetic member 26 is provided on the other end of each swing arm 25 with a predetermined distance from the electromagnetic device 27. The inside of the pump housing 21 is divided into two chambers; a first chamber 211 in the upper portion and a second chamber 212 in the lower portion. Although the first chamber 211 and the second chamber 212 are arranged upper-and-lower in this preferred embodiment, the two chambers could also be arranged forward-and-back. The first chamber 211 is communicated with one or more inlet tubes 22 and the second chamber 212 is communicated with one or more outlet tubes 23. Two check valves 241 and 242 are respectively provided between the sides of the chamber 211, chamber 212 and the bladders 24. Due to the reciprocating swinging of the swing arms 25, the electromagnetic pump 20 draws fluid into the chambers from the inlet tubes 22 and then discharges the fluid from the outlet tubes 23. The theory of the movement of the electromagnetic pump 20 will not be mentioned as it has already been illustrated in FIGS. 2 to 7.

Figure 1:
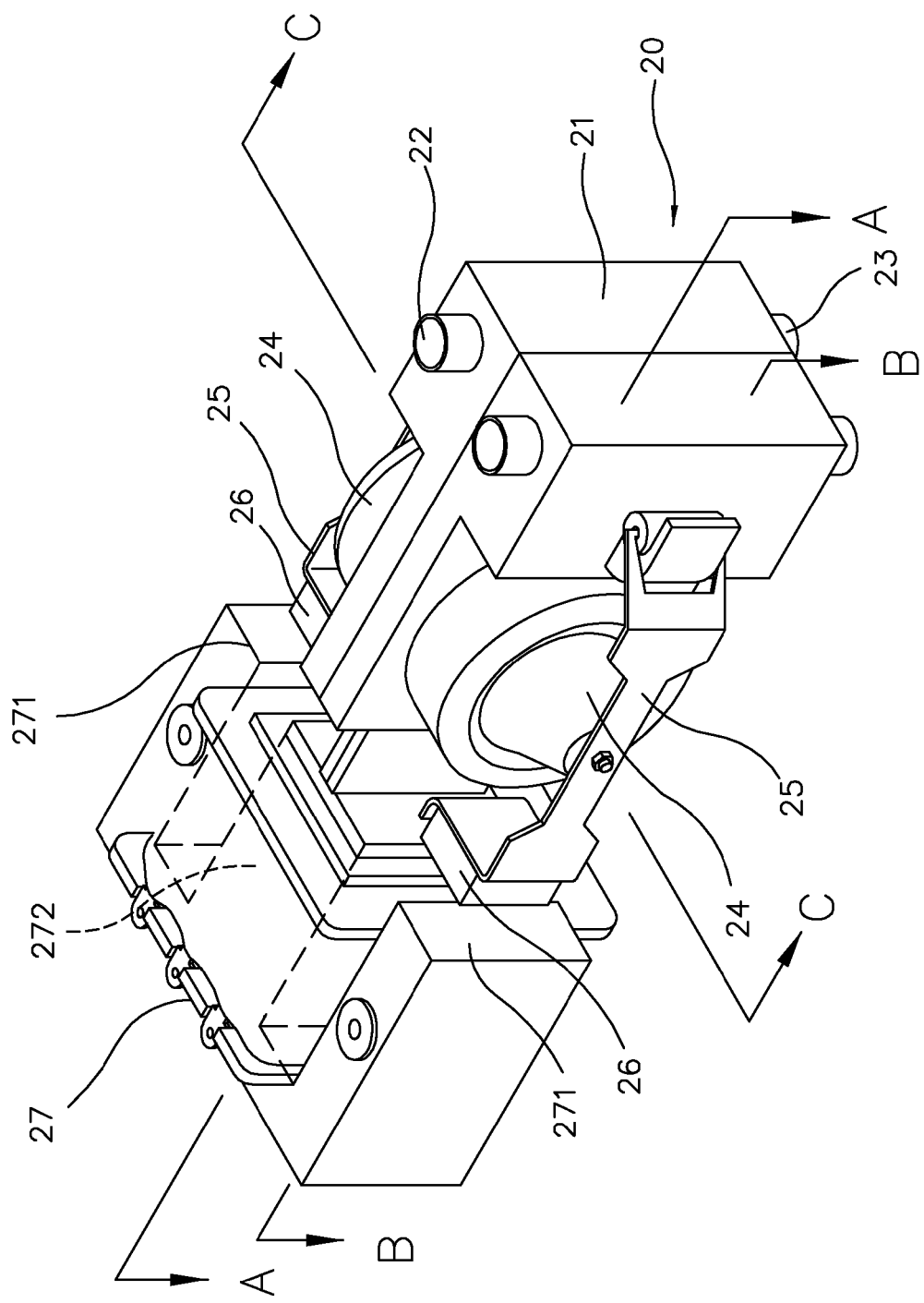
FIG. 1 is a schematic diagram of an electromagnetic pump according to a preferred embodiment of the present invention.
Figure 2:
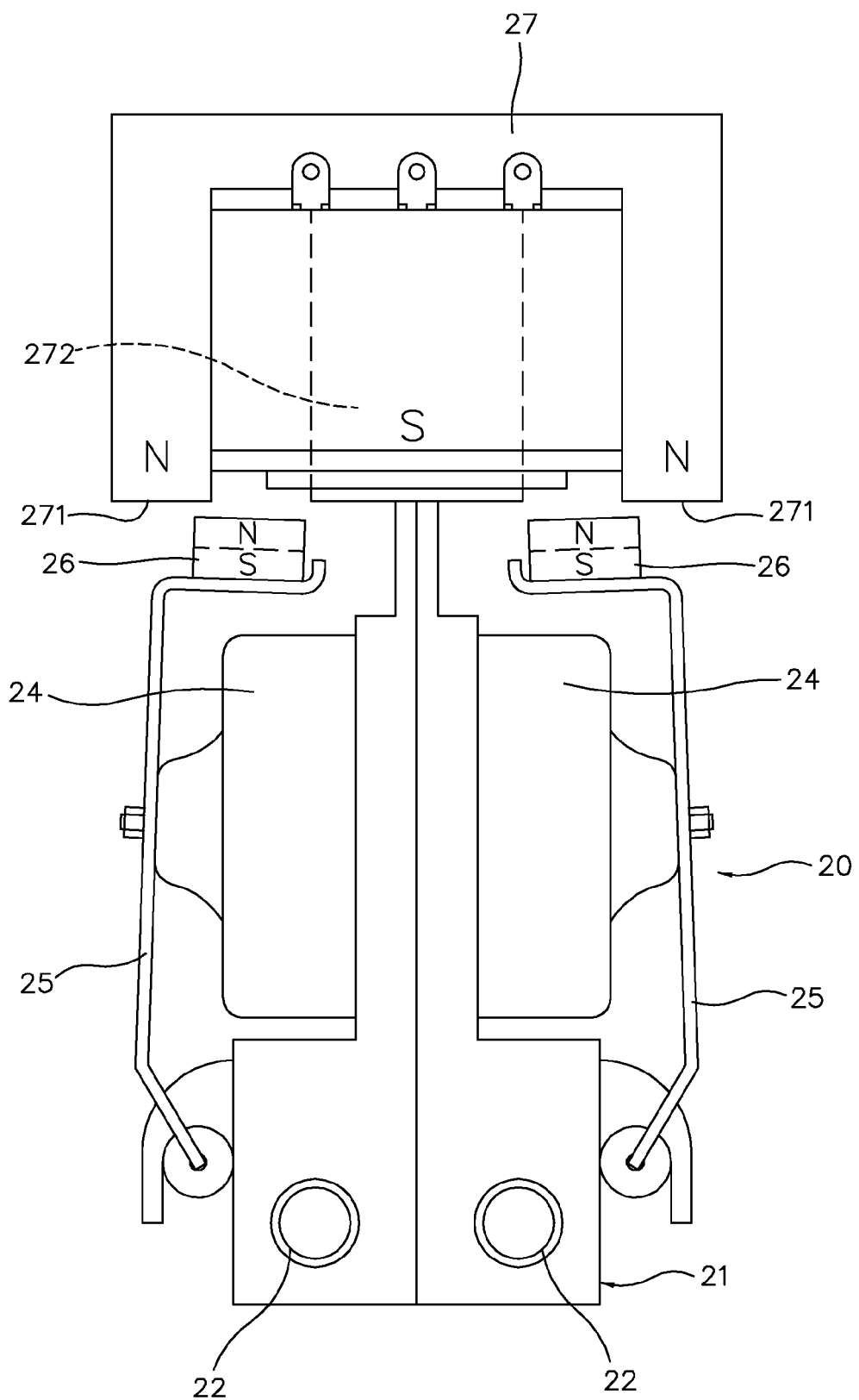
FIG. 2 is a schematic diagram of the electromagnetic with the swing arms swinging inward according of FIG. 1.
Figure 3:
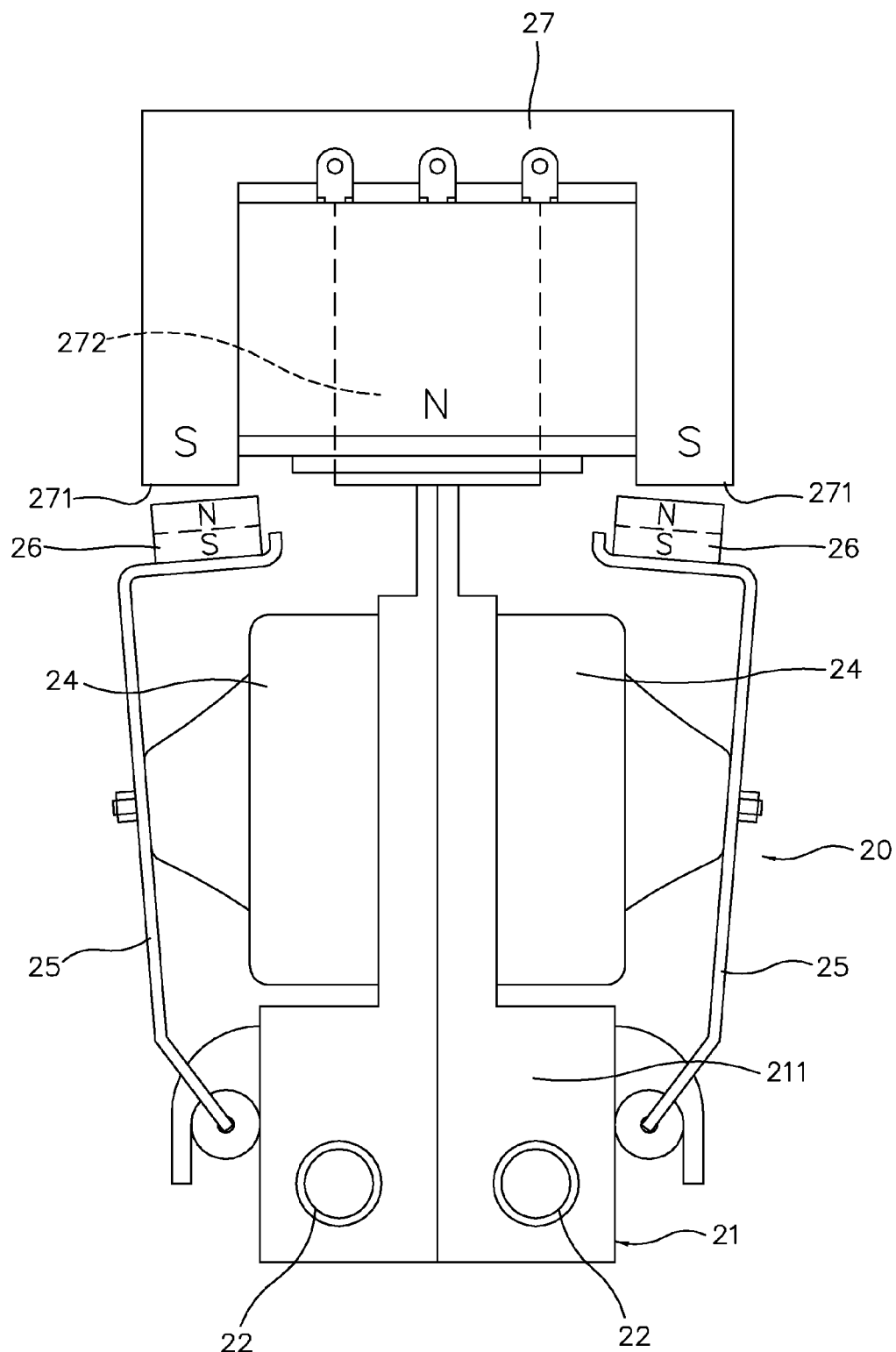
FIG. 3 is a schematic diagram of the electromagnetic with the swing arms swinging outward of FIG. 1.
Figure 4:
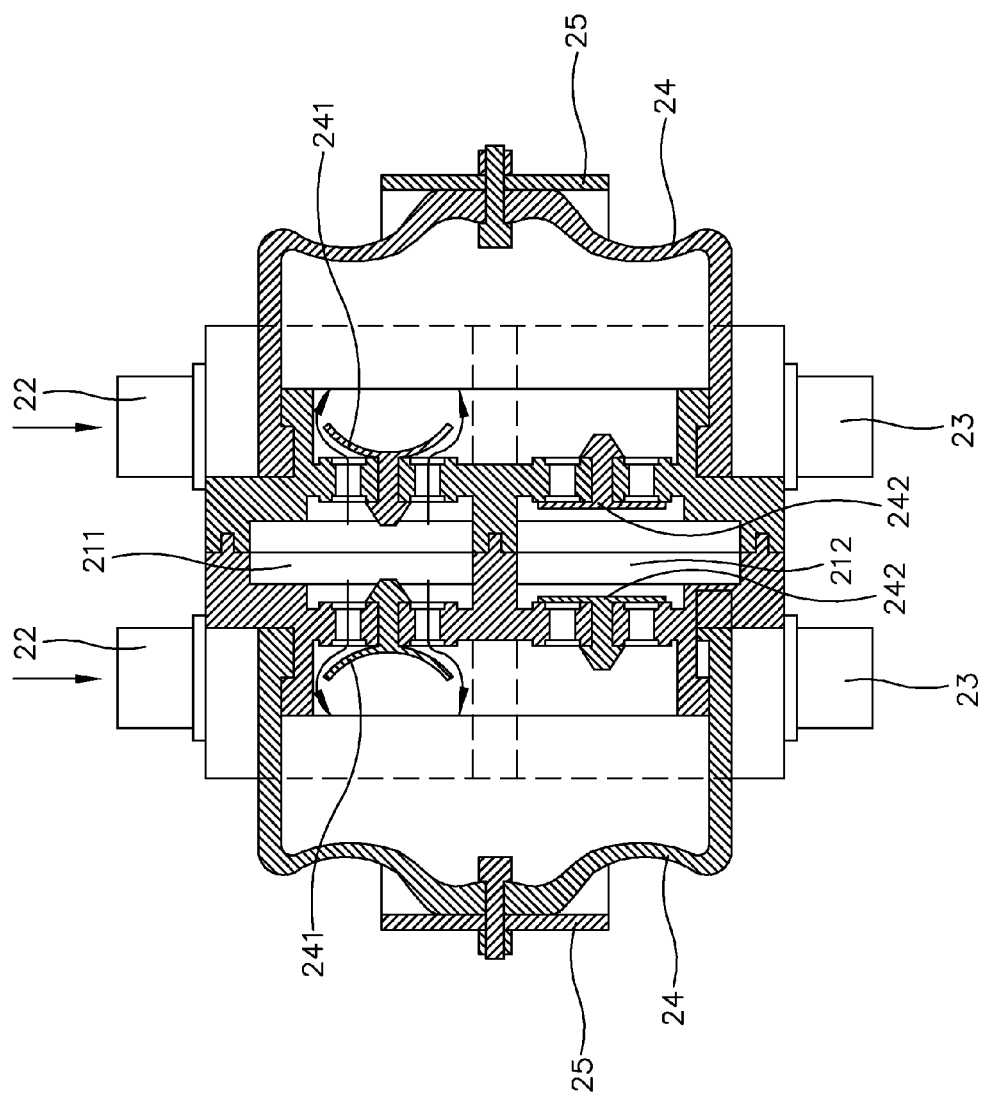
FIG. 4 is a C-C section view of the electromagnetic pump of FIG. 1 illustrating the flow direction of the fluid drawn by the electromagnetic pump.
Figure 5:
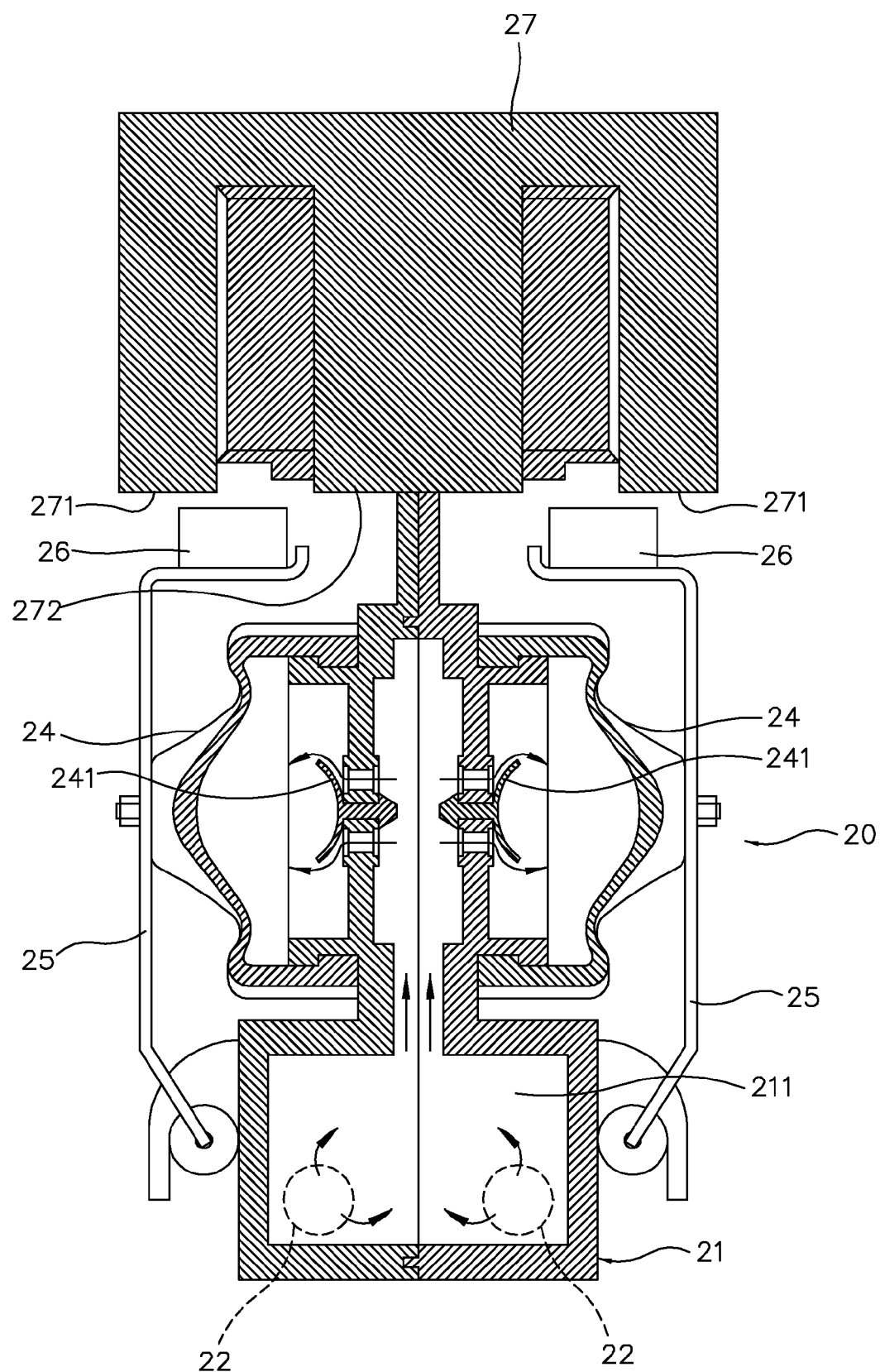
FIG. 5 is an A-A section view of the electromagnetic pump of FIG. 1 illustrating the flow direction of the fluid drawn by the electromagnetic pump.
Figure 6:
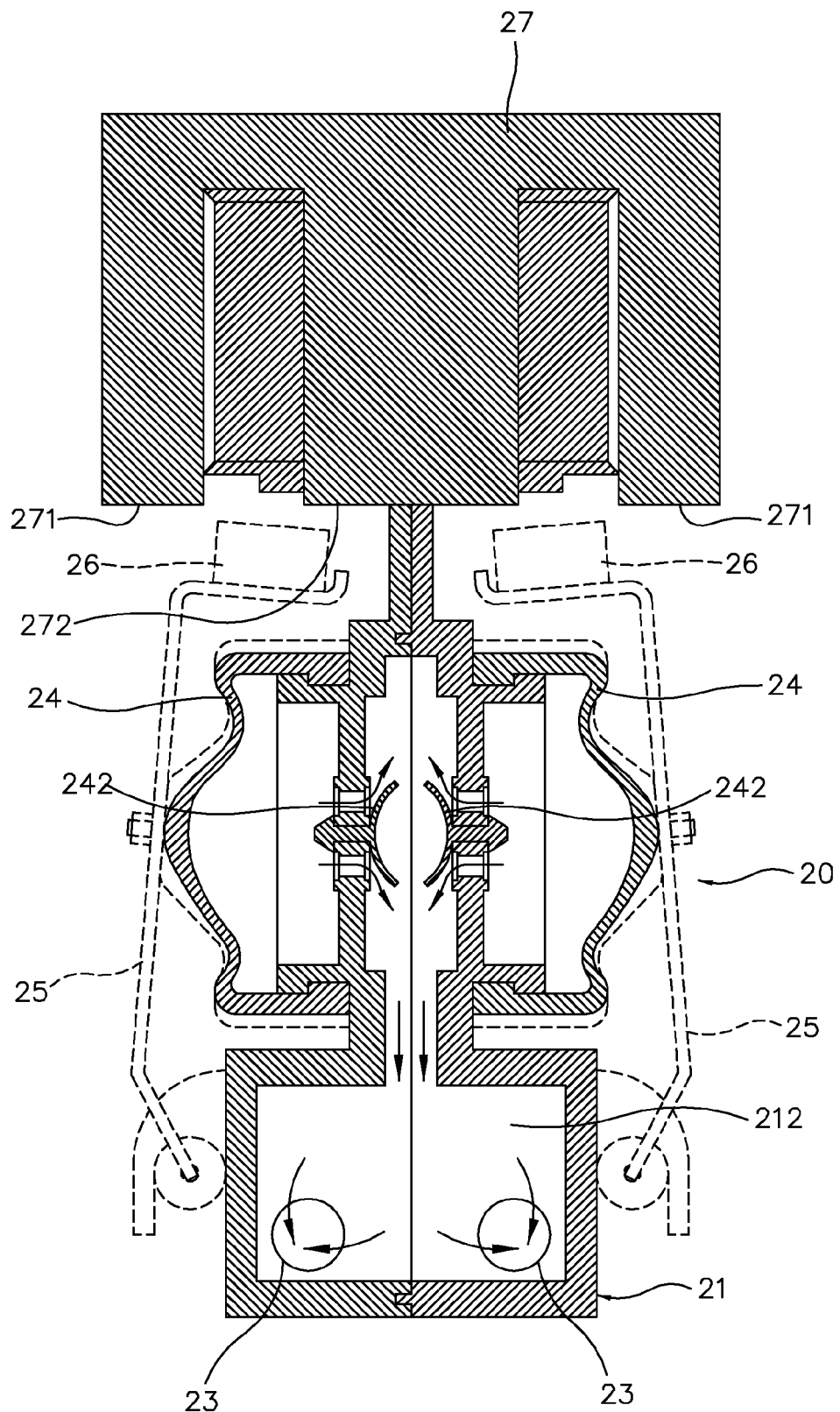
FIG. 6 is a B-B section view of the electromagnetic pump of FIG. 1 illustrating the flow direction of the fluid discharged by the electromagnetic pump.
Figure 7:
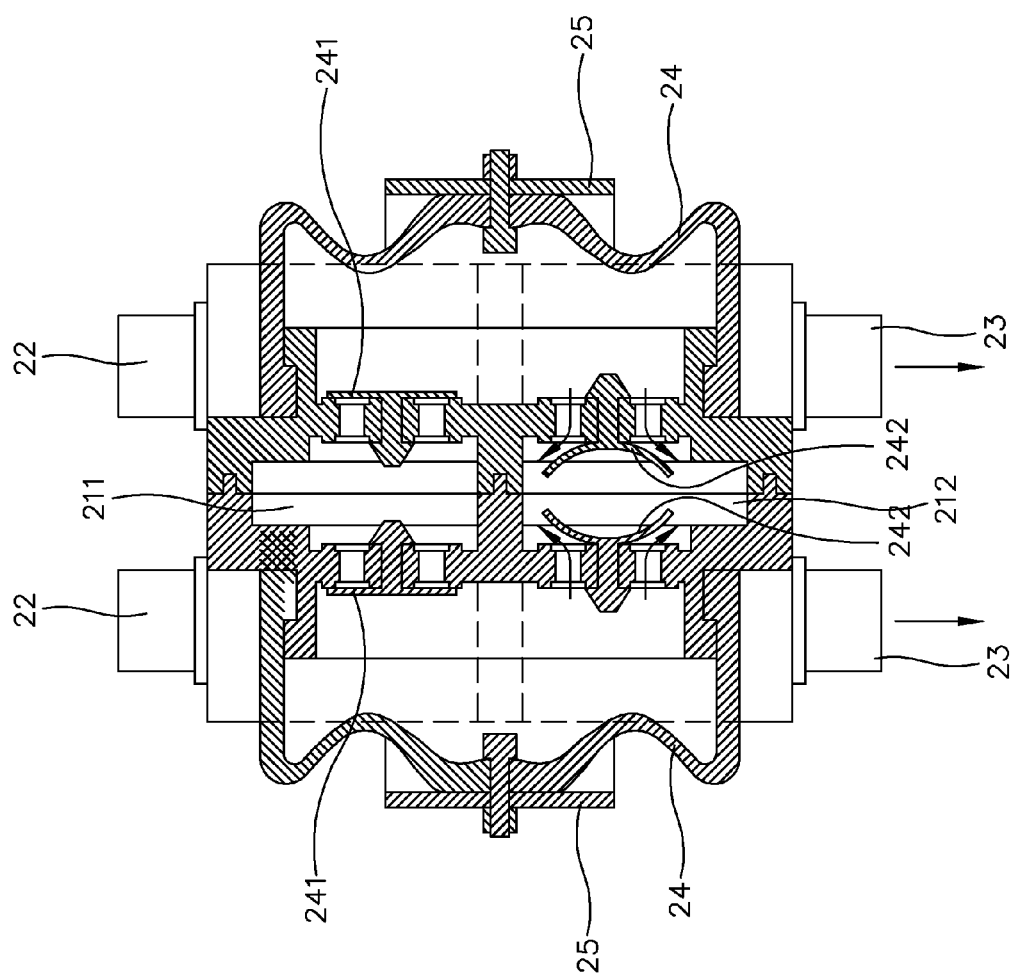
FIG. 7 is a C-C section view of the electromagnetic pump of FIG. 1 illustrating the flow direction of the fluid discharged by the electromagnetic pump.
Figure 8:
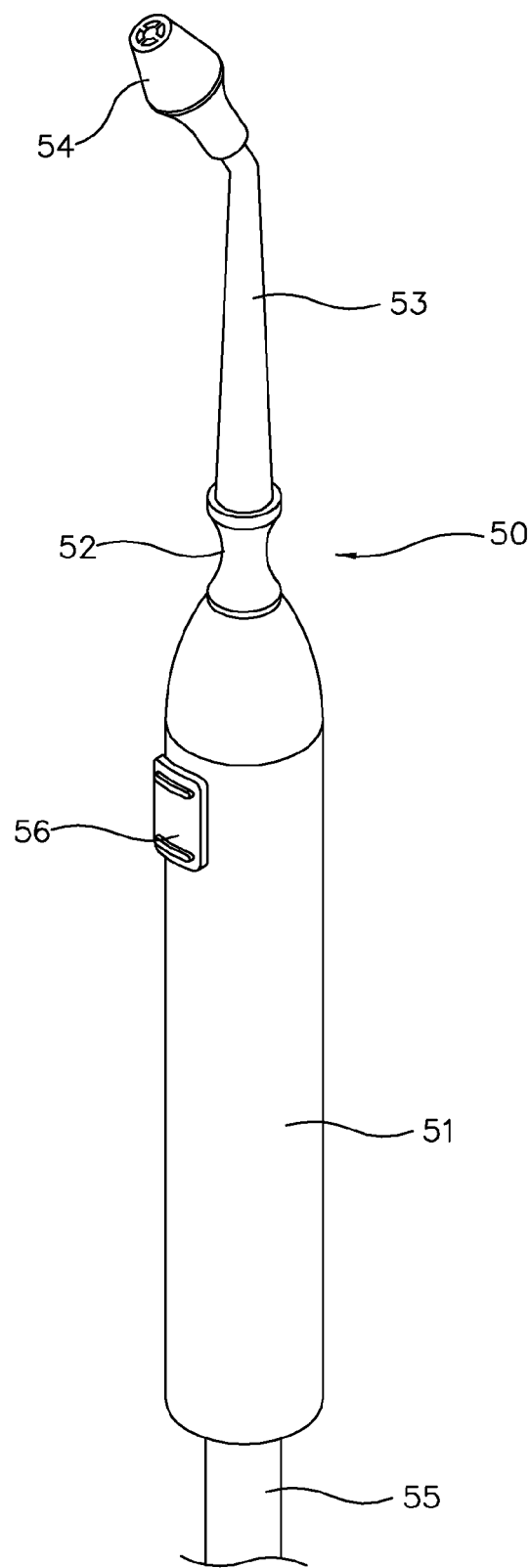
FIG. 8 is a perspective view of a nose-washing tool according to the prior art.
Figure 9:
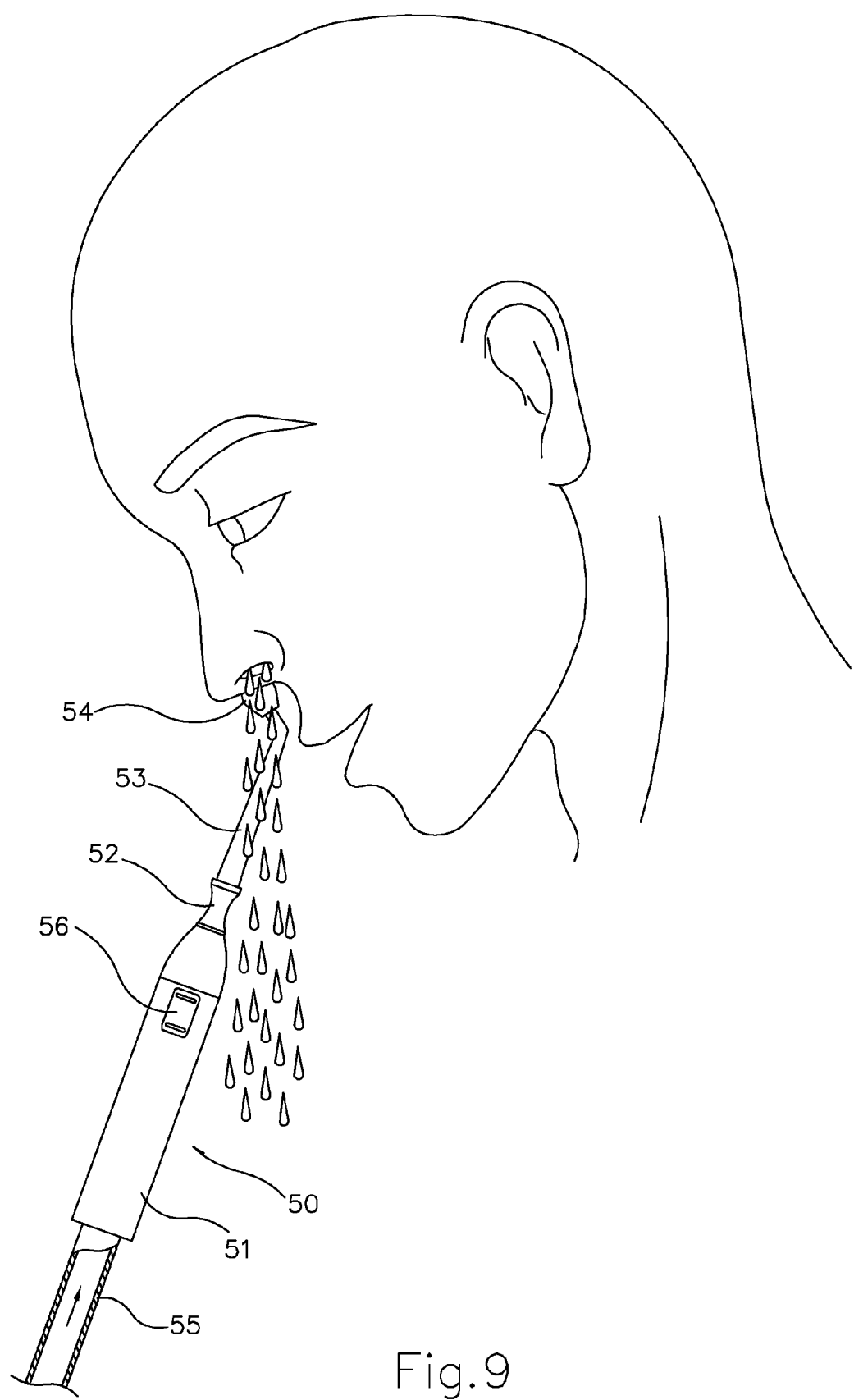
FIG. 9 is a perspective view of a nose-washing tool when using according to the prior art.

A fluid container 1, as shown in FIG. 1, has a containing space 11, therein for storing a cleaning solution, and an upper opening enabling an upper cover 12 to cover thereon. The upper cover 12 has a connecting member 13 provided thereon for communicating with the electromagnetic pump 20 through a negative pressure channel 31. A suction member 14, made of soft material, is connected to the bottom of the connecting member 13 for providing the cleaning solution stored in the containing space 11 of the container 1 as a fluid source according to the present invention.

Figure 13:
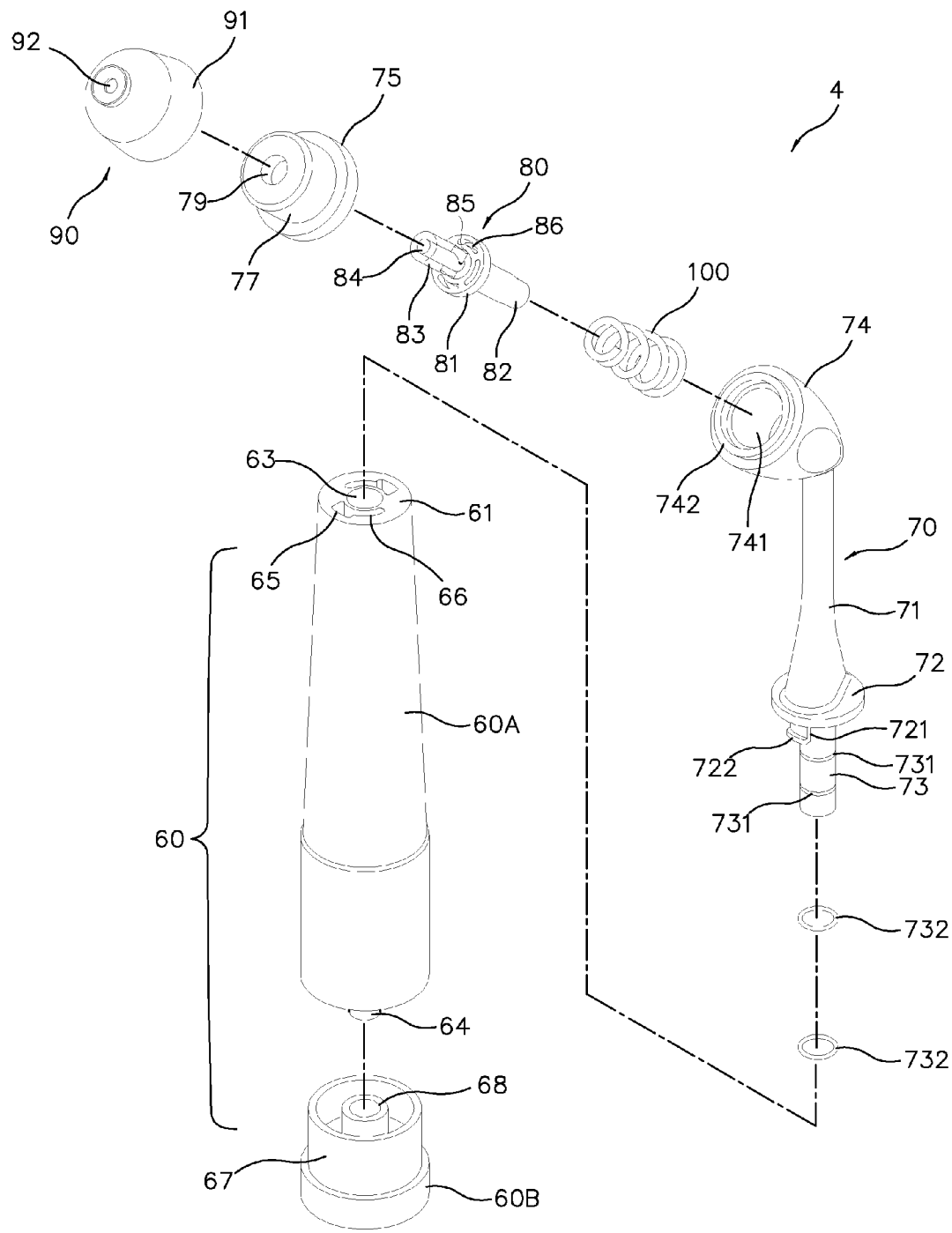
FIG. 13 is an exploded perspective view of the nose-washing tool according to the above preferred embodiment of the present invention.
Figure 14:
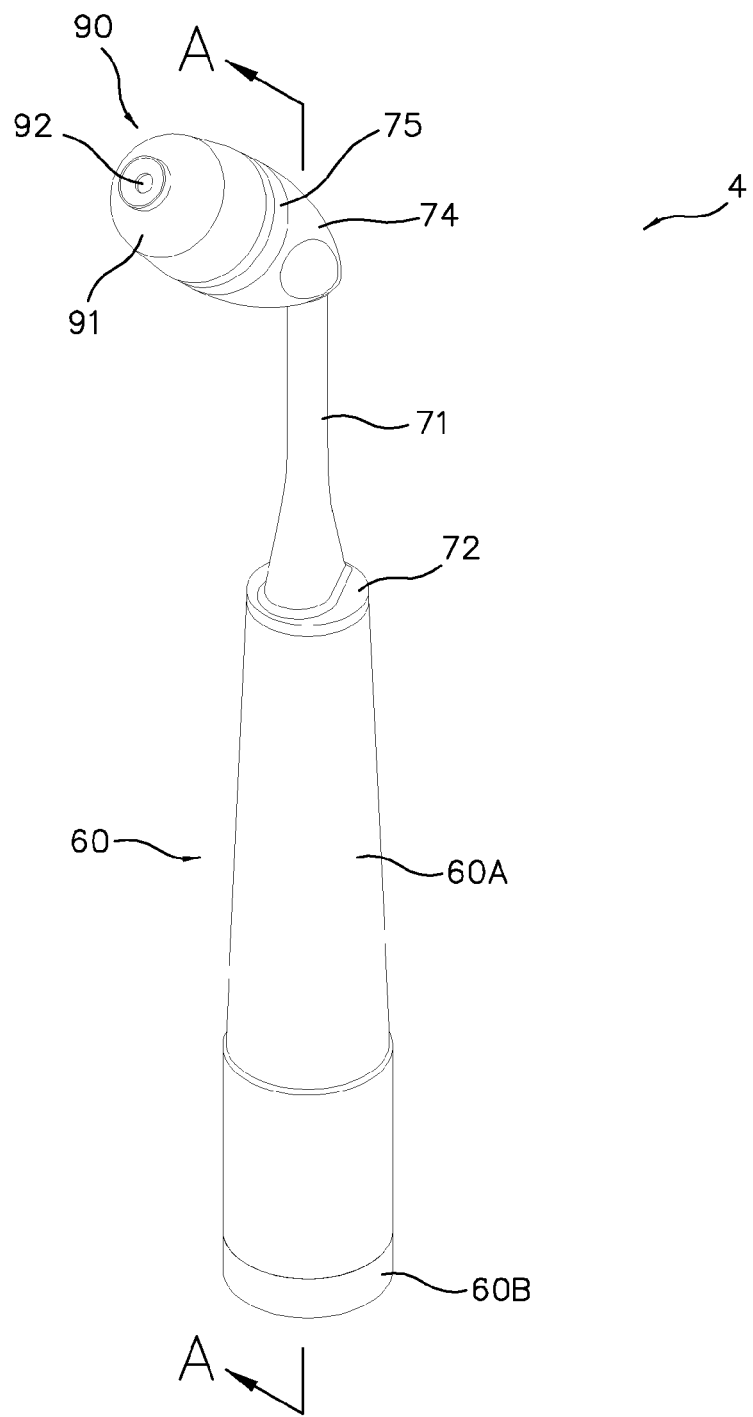
FIG. 14 is an assemble view of the nose cleaner of FIG. 13.
Figure 17:
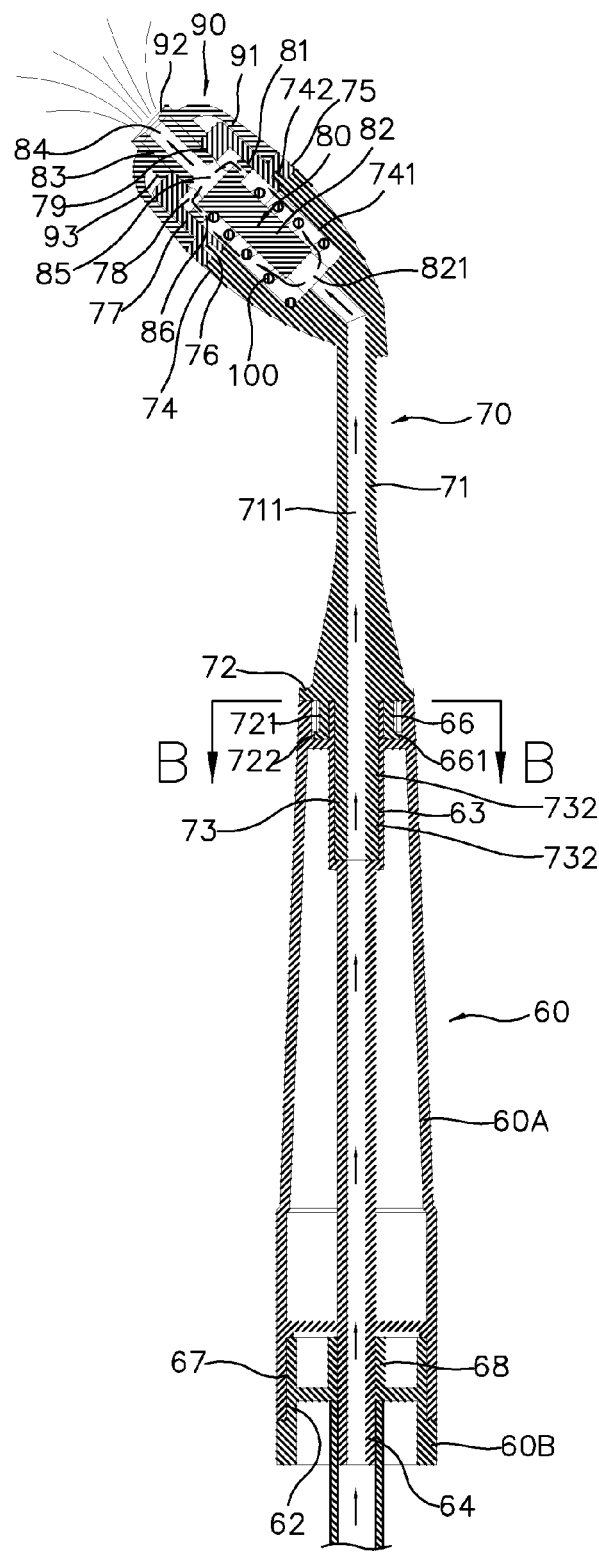
FIG. 17 is an A-A section view of the nose-washing tool of FIG. 14.
Figure 18A:
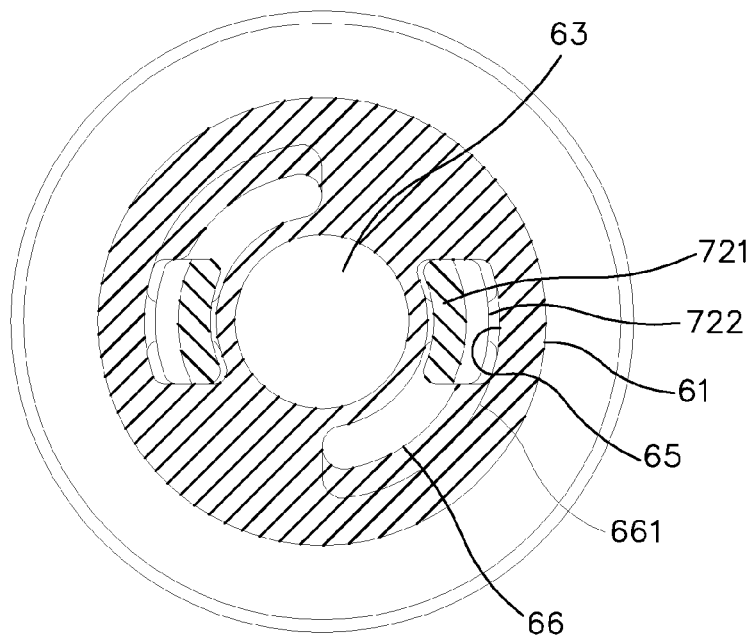
FIGS. 18A and 18B are schematic diagrams illustrating the assembling of the extension tube and the handle of the nose-washing tool according to the above preferred embodiment of the present invention.
Figure 18B:
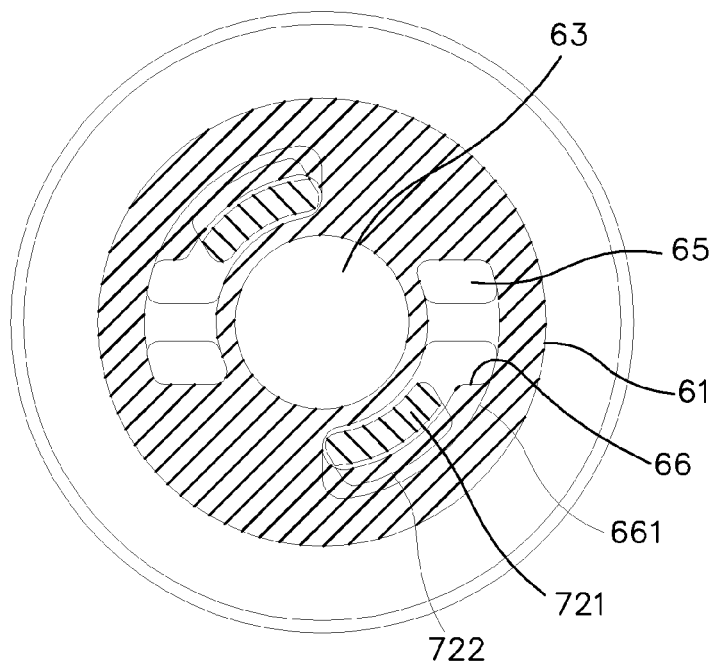

As illustrated in FIGS. 13 and 17, the nose-washing tool 4 has a handle 60, which comprises a hollow channel 60A and a base 60B. The hollow channel 60A has a platform 61 on the top end, a trepan boring 62 opened downwardly on the bottom edge, an insert channel 63 disposed in the center portion of the platform 61 and extended into the hollow channel 60A, and a connecting channel 64 with a smaller hole diameter coaxially connected on the bottom of the insert channel 63; wherein the bottom portion of the connecting channel 64 is exposed outside the bottom of the hollow channel 60A. Referring to FIGS. 18A and 18B, the platform 61 has two arcuate insert grooves 65 and two arcuate block grooves 66, which are symmetrically arranged on the platform 61 and centered on the insert channel 63, respectively; wherein the arcuate insert grooves 65 are respectively communicated with the arcuate block grooves 66. The arcuate block groove 66 has a groove width smaller than that of the arcuate insert groove 65 and has an arcuate resist groove 661 disposed on the bottom thereof, wherein the arcuate resist groove 661 has the same groove width as that of the arcuate insert groove 65. The base 60B has a covering member 67 mated with the trepan boring 62, a channel base 68 for the connecting of channel 64. Drilling through to make the base 60B could assist and support the end of the connecting channel 64 so that the fluid inlet tube could solidly connected with the end of the connecting channel 64 to transport the cleaning solution into the connecting channel 64.

Figure 15:
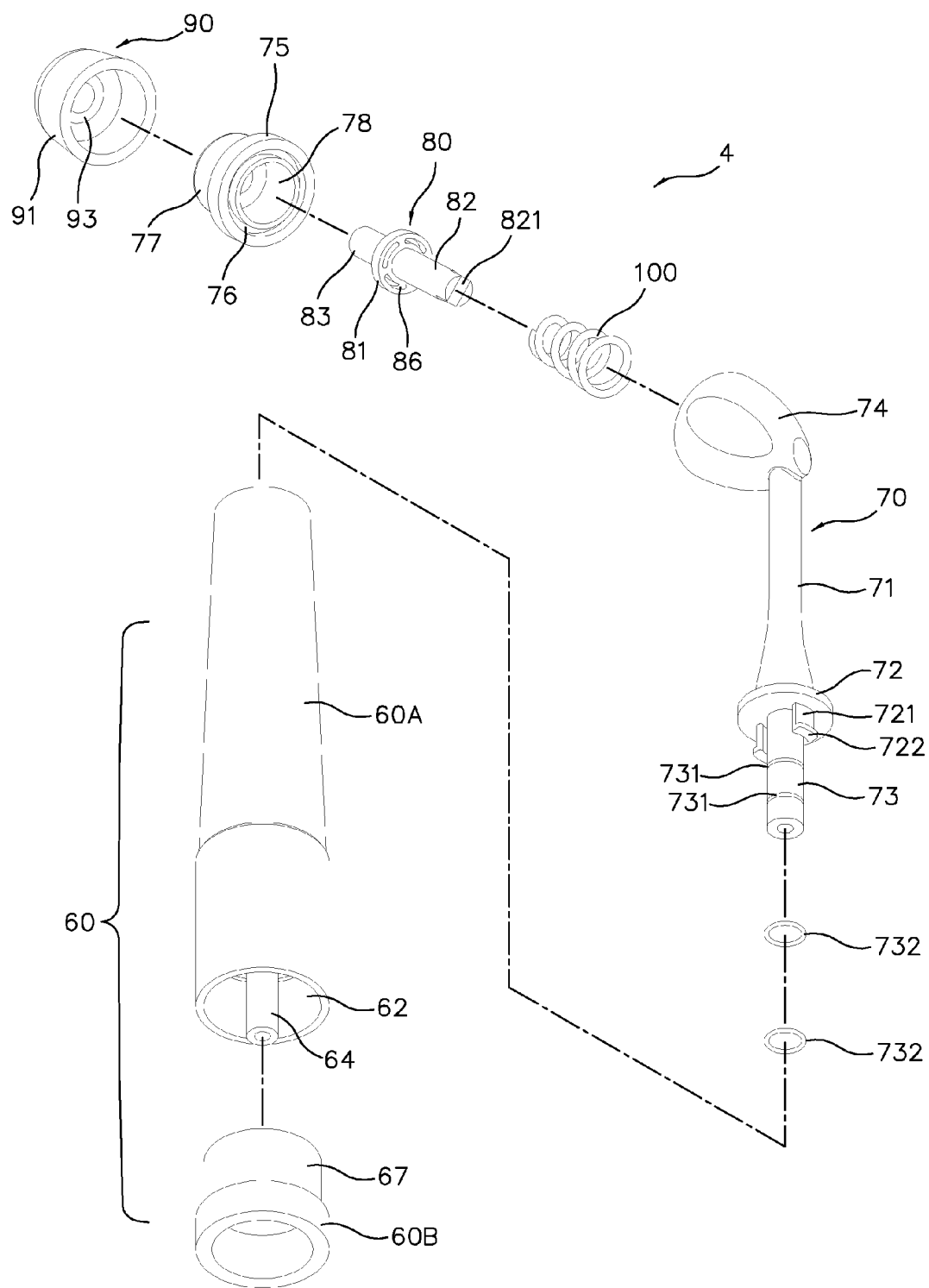
FIG. 15 is another exploded perspective view of the nose-washing tool according to the above preferred embodiment of the present invention.
Figure 16:
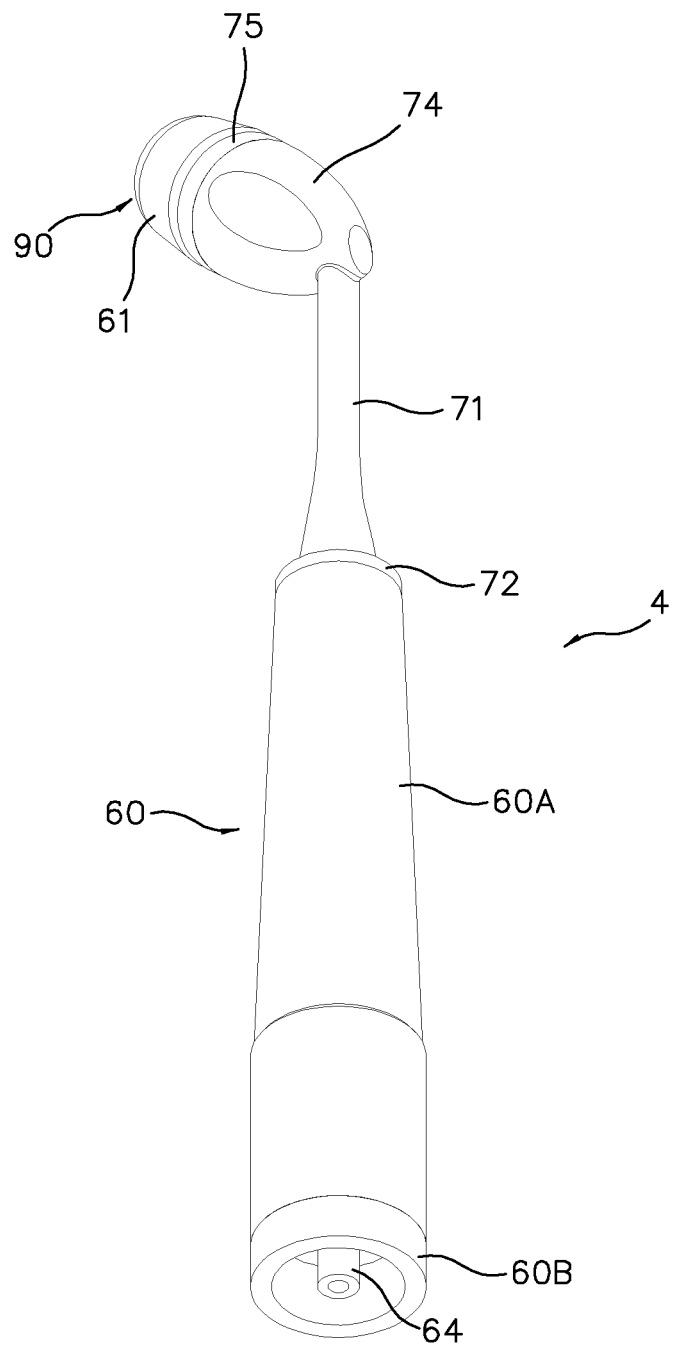
FIG. 16 is an assemble view of the nose cleaner of FIG. 15.

As illustrated in FIGS. 13, 15 and 17, extension channel 70 has a channel body 71, a fixing base 72 disposed on the bottom of and extruded along the radial direction of the channel body 71 and mated with the platform 61, a receiving channel 73 disposed on the bottom of the fixing base 72 and mated with the insert channel 63, and a head 74 disposed on the top of the channel body 71. Referring to FIGS. 18A and 18B, the fixing base 72 has two arcuate plates 721 and two arcuate blocks 722 respectively disposed on the bottom of the arcuate plates 721 and radically extruded therefrom. The two arcuate plates 721 and the two arcuate blocks 722 could respectively insert into the arcuate insert grooves 65 and rotate toward the arcuate block grooves 66. As a result, the arcuate blocks 722 are respectively located inside of the arcuate resist grooves 661 on the bottom of the arcuate block grooves 66, wherein the extension channel 70 could be quickly assembled with the handle 60. For the same reason, if the extension channel 70 needs to be changed, the extension channel 70 only needs to be rotated backward to make the arcuate plates 721 and the arcuate blocks 722 respectively face the arcuate insert grooves 65; then the extension channel 70 could be drawn out upward. The receiving channel 73 has a ring groove 731 disposed on the outside surface thereof, which could be engaged with an O shaped ring 732 to make the receiving channel 73 connect tightly with the insert channel 65 without leakage. An inner hole 711 is formed inside of the channel body 71 and the receiving channel 73, wherein the inner hole 711 is communicated with the connecting channel 64 and has the same diameter as the connecting channel 64. The head 74 has a containing house 741 grooved at the end thereof and engaged with the top end of the inner hole 711, thereby the containing house 741 receives the cleaning solution that flows in from the receiving channel 64. The head 74 has a ring block 742 protruded at the end.

Referring to FIGS. 13, 15 and 17, a fixing head 75 has a ring slot 76 mated with the ring block 742 to cause a guiding house 78 to be formed inside of the fixing head 75, wherein the guiding house 78 is communicated with the containing house 741. The head 77 further has a fluid outlet hole 79 disposed on the top and in the center of the top, wherein the fluid outlet hole 79 communicates the inner side and the outer side of the guiding house 78.

Referring to FIGS. 13, 15, 17 and 19A, a touch sensitive switch 80 has a shoulder member 81 that slides along the guiding house 78, wherein a center shaft 82 is extended downwardly from the center of the shoulder member 81. In order to avoid the bottom of the center shaft that blocks the top of the inner hole 711 in the extension channel 70, the center shaft 82 has a groove 821 disposed on the bottom. The shoulder member 81 has a spindle 83 disposed on the top thereof and extended upwardly from the center thereof in such a manner that the spindle 83 could move back and forth in the fluid outlet hole 79. The spindle 83 further has a spray hole 84 provided on the top and a fluid guiding hole 85 radically provided on a portion towards the shoulder 81, wherein the fluid guiding hole 85 is communicated with the spray hole 84, and the shoulder member 81 is communicated with the guiding house 78 and a hole 86 of the containing house 741. The spindle 83 further has a hollow spray nozzle 90 disposed on the top thereof. The spray nozzle 90 has a ring cover 91 arranged to cover the head 77, a sleeve 93 engaged with the top of the spindle 83, a through-hole 92 communicated the inner side, and the outer side of the spray hole 84, wherein the spray nozzle 90 could also slide along the head 77.

A resilient element, which is embodied as a spring 100 in the preferred embodiment of the present invention, has an end supported on the bottom of the containing house 741 and another end supported on the shoulder member 81 while the center shaft 82 is sleeved in and extended along the spring 100. The shoulder member 81 is supported onto the inner top surface of the guiding house 78 due to the force of the spring 100, thereby the hole 86 is closed by the inner top surface of the guiding house 78, and the fluid guiding hole 85 is closed by the inner surface of the fluid outlet hole 79.

Figure 19B:
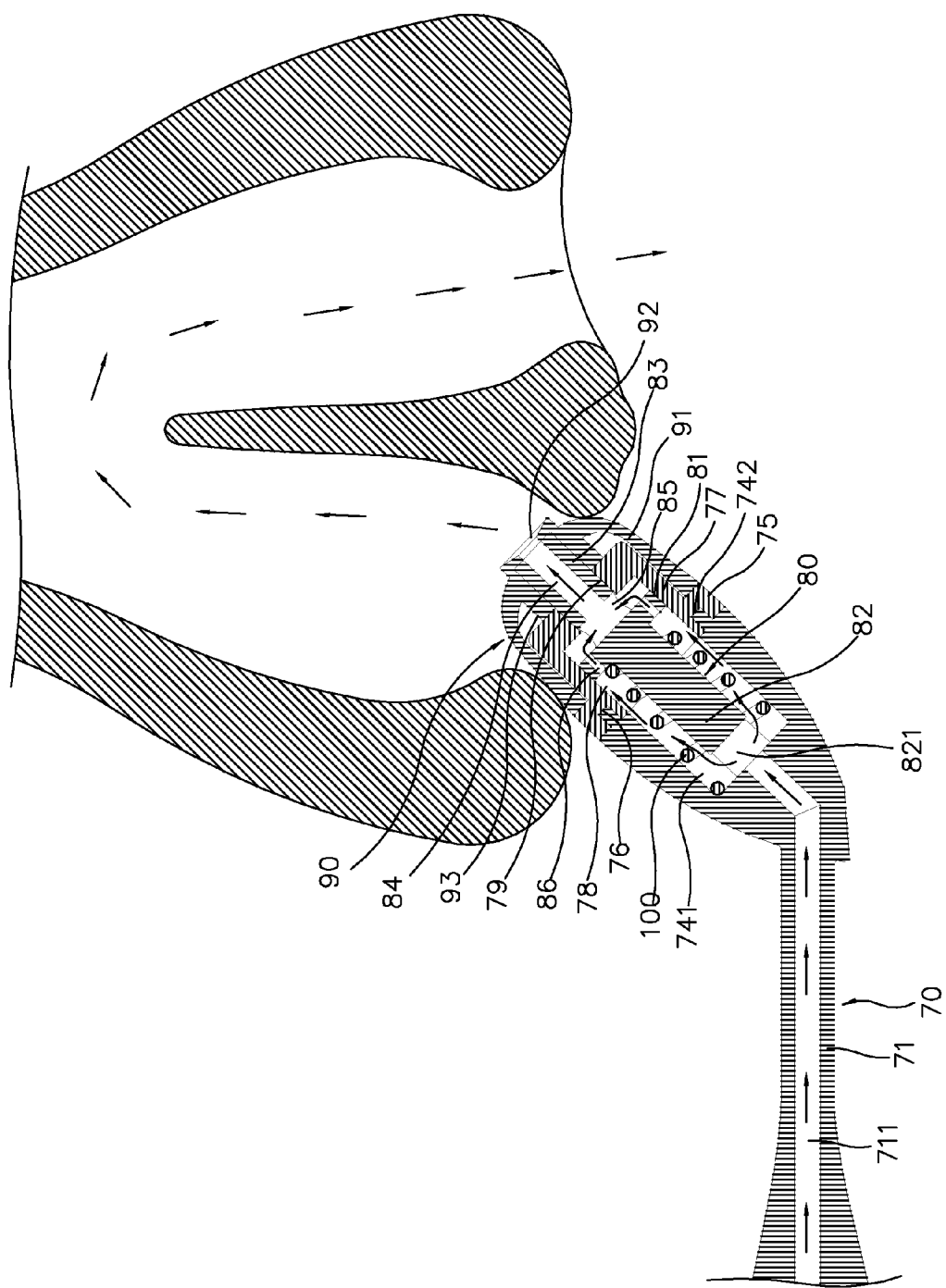
FIG. 19B is a partial enlarged view of the nose-washing tool in open condition for cleaning the nasal cavity.

Referring to FIGS. 13, 19A and 19B, when the spray nozzle 90 touches the nasal cavity, the spindle 83 of the touch sensitive switch 80 is brought to move, and the shoulder member 81 overcomes the predetermined force of the spring 100 and moves towards the containing house 741, thereby the hole 86 and the fluid guiding hole 85 could be communicated with each other through the guiding house 78. The cleaning solution in the containing house 741 is transported to the spray hole 84 and injected out from the through-hole 92 of the spray nozzle 90, thereby the function of cleaning nasal cavity could be achieved. When the user chokes due to the nasosinusitis or the incapability of autonomous respiration, the user merely needs to draw the spray nozzle 90 out from the nasal cavity, and the spring 100 will elastically comeback and force the touch sensitive switch 80 to close the hole 86 by the inner top surface of the guiding house 78 and close the fluid guiding hole 85 by the inner surface of the fluid outlet hole 79, thereby the cleaning solution injected from the spray nozzle 84 will be immediately turned off. Therefore, the defect that the cleaning solution injecting here and there has been overcome.

The frequency converter circuit 40 comprises a voltage reduction circuit 42, an oscillator circuit 43, a bi-stable circuit 44, and a push-pull circuit 46. The voltage reduction circuit 42 transforms the 12V DC inputted by the outside DC power source 41 to 5V DC, which is supplied to each circuit as the working current, wherein the voltage reduction circuit 42 could be used to stabilize the voltage. The oscillator circuit 43 could be a Schmitt oscillator circuit, which oscillates to transform a 12V DC into a single-phase oscillating signal with an oscillating frequency between 43 Hz and 66 Hz. The bi-stable circuit 44 splits the single-phase oscillating signal into an N-phase stimulus signal and an S-phase stimulus signal, both of which respectively activate the magnetism of the two side magnetic members 271 and the middle magnetic member 272 to alternate switching between the N-phase and S-phase. Accordingly, the two side magnetic members 271 and the middle magnetic member 272 are attracted or repulsed by the two magnetic members 271 respectively to force the swing arms 25 to reciprocate to compress or expand the bladders 24 respectively. The push-pull circuit 46 amplifies the N-phase stimulus signal and the S-phase stimulus signal to force the swing arms 25 of the electromagnetic pump 20 to swing effectively to further improve the power of the electromagnetic pump 20.

Figure 12A:
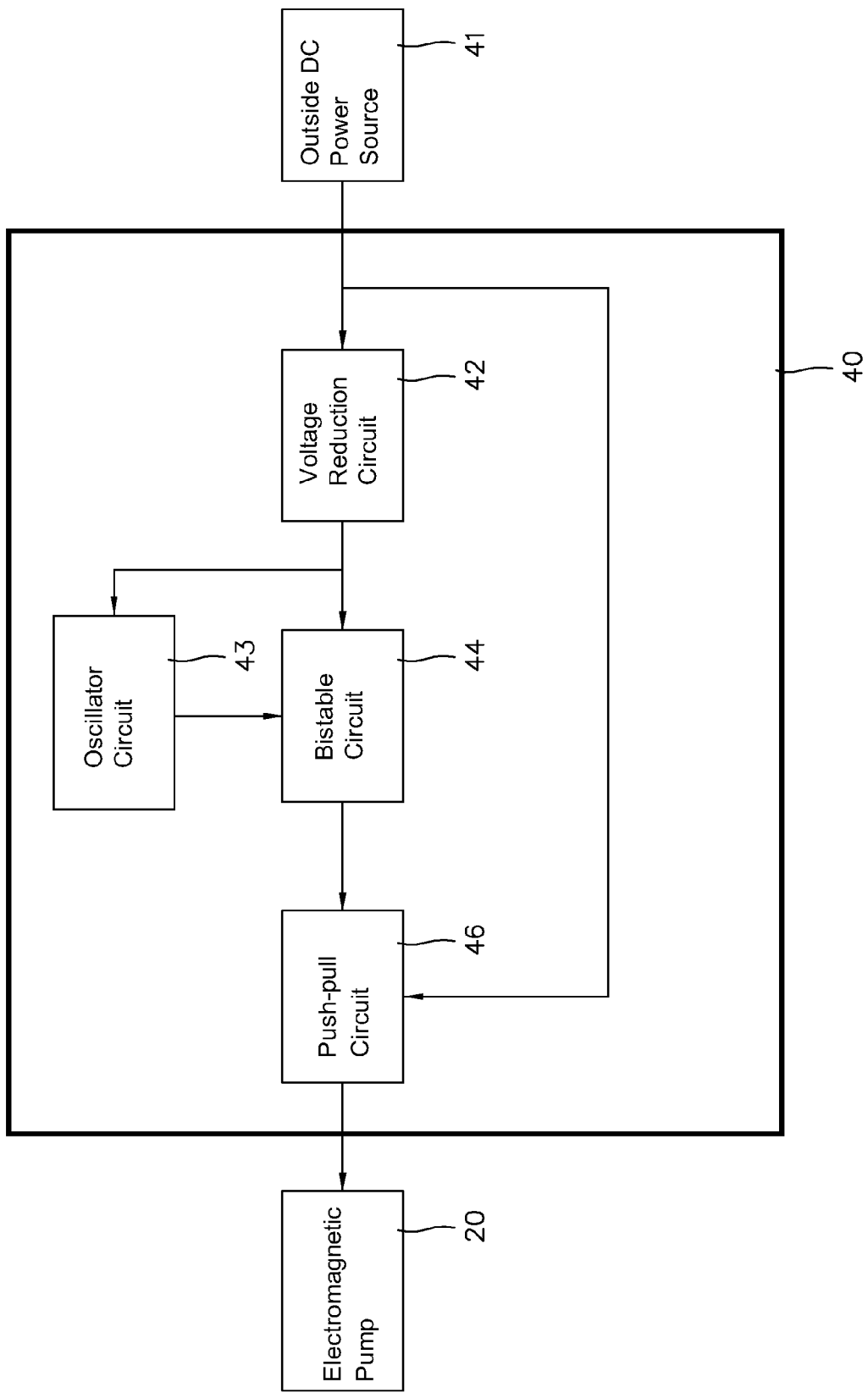
FIG. 12A is a block flow chart of a frequency converter circuit according to the above preferred embodiment of the present invention.
Figure 12B:
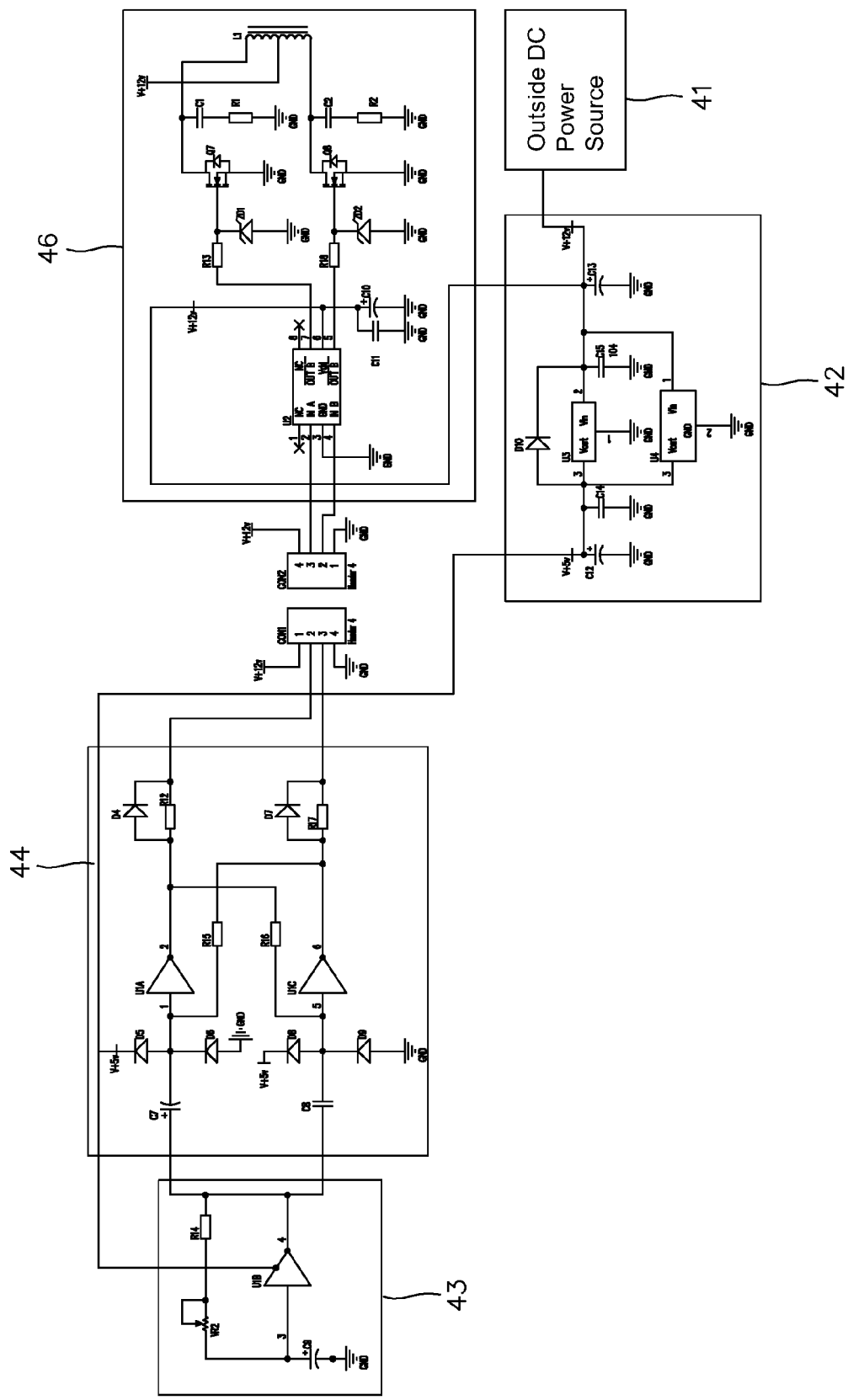
FIG. 12B is a circuit diagram of the circuit of FIG. 12A.
Figure 20:
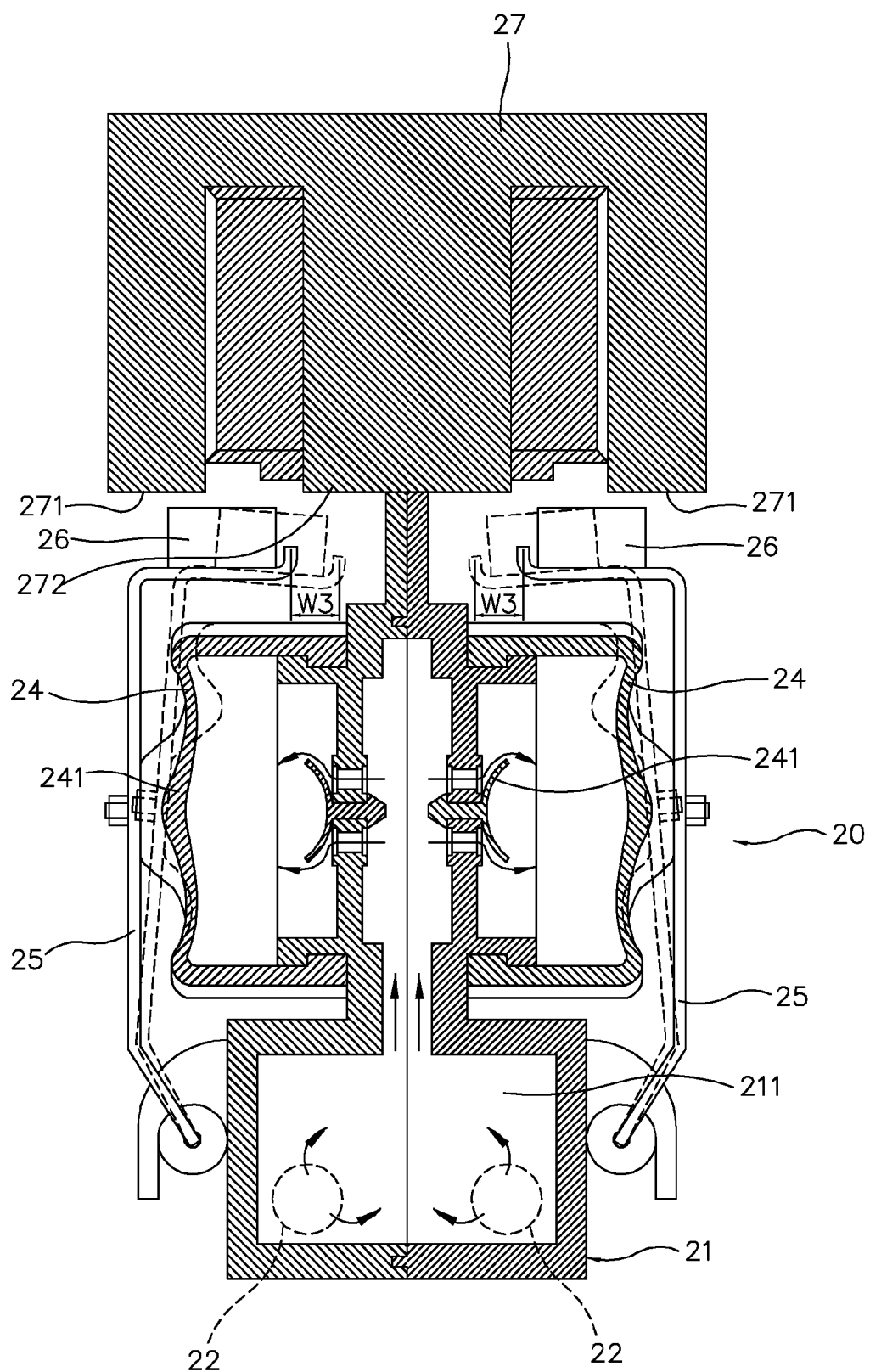
FIG. 20 is a schematic diagram of the electromagnetic pump according to the above preferred embodiment of the present invention illustrating the swinging of the swing arms with minimum frequency and maximum amplitude W3.
Figure 21:
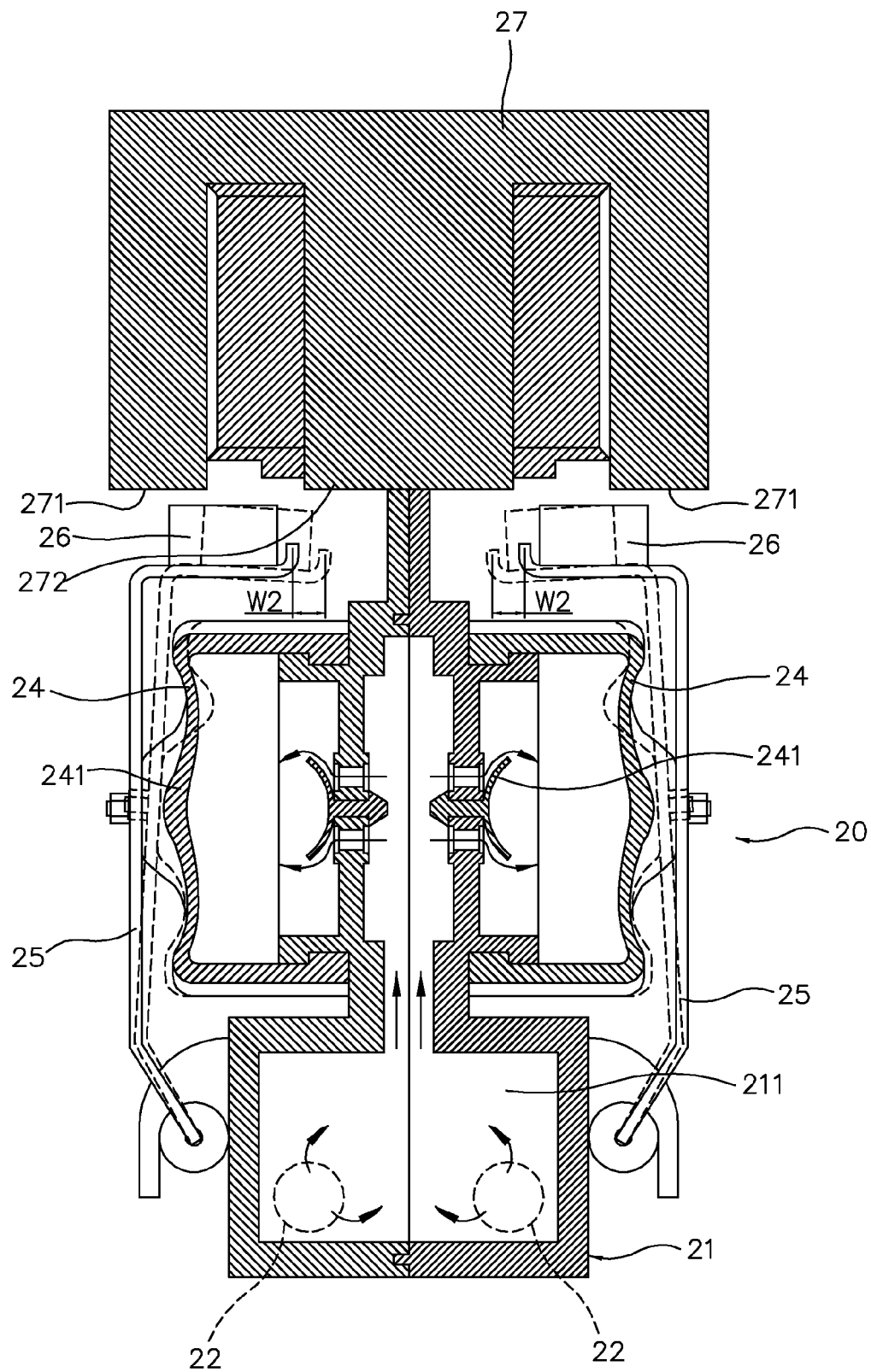
FIG. 21 is a schematic diagram of the electromagnetic pump according to the above preferred embodiment of the present invention illustrating the swinging of the swing arms with medium frequency and medium amplitude W2.
Figure 22:
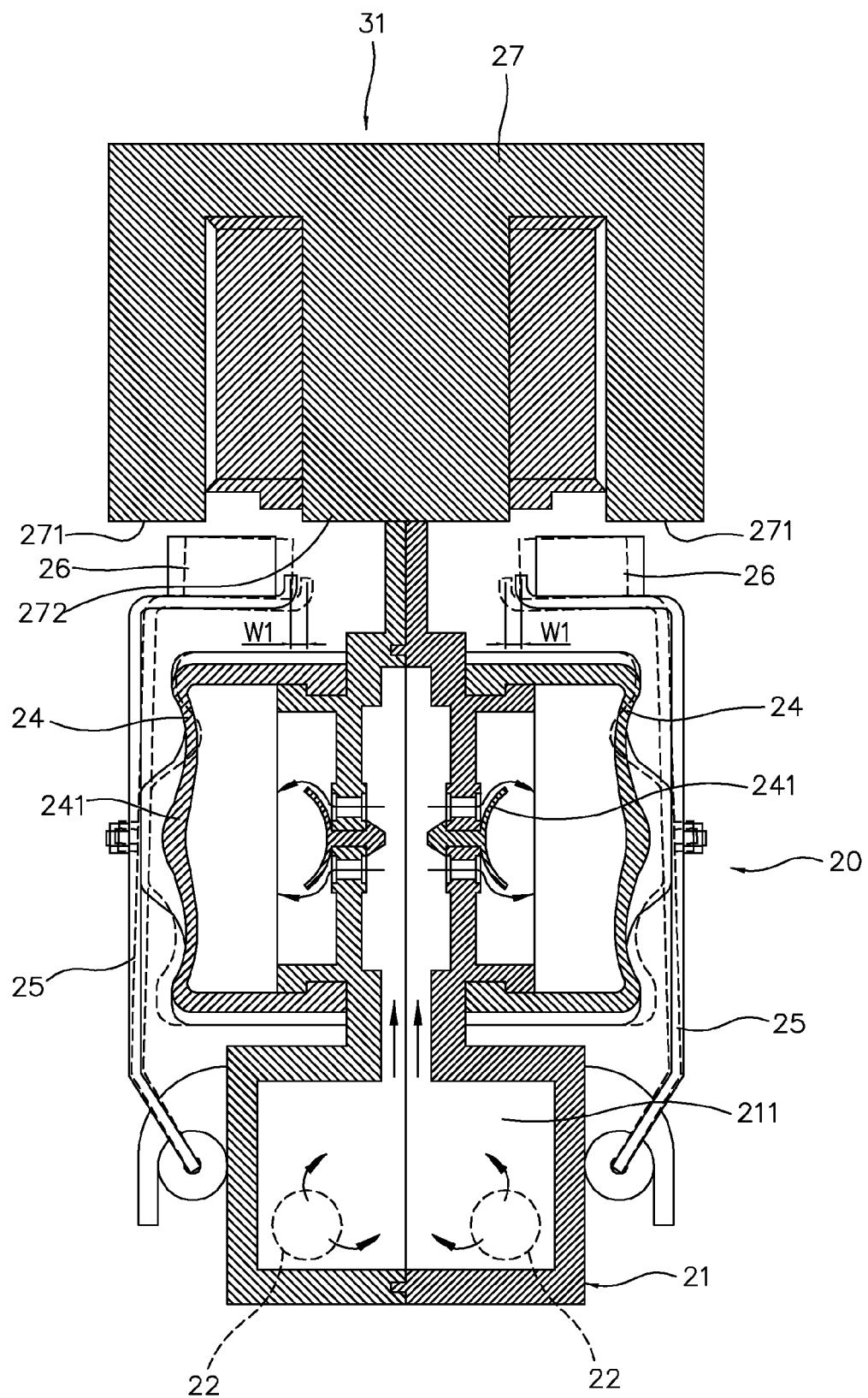
FIG. 22 is a schematic diagram of the electromagnetic pump according to the above preferred embodiment of the present invention illustrating the swinging of, the swing arms with maximum frequency and minimum amplitude W1.

Referring to FIGS. 20 to 22, when the oscillator frequency of the oscillator circuit 43 is adjusted to a low frequency such as 43 Hz, the speed of the switching between the N-phase and the S-phase of the electromagnetic device 27 decreases to further cause the reciprocated swinging of the swing arms 25 to have a lower speed, a lower frequency, and larger amplitude; shown as W3 in FIG. 12. Due to the decrease of the swing speed of the swing arms 25, the discharge pressure of the electromagnetic pump 20 decreases, and due to the increase of the swing amplitude of the swing arms 25, the discharge flow of the electromagnetic pump 20 increases substantially.

Figure 23:
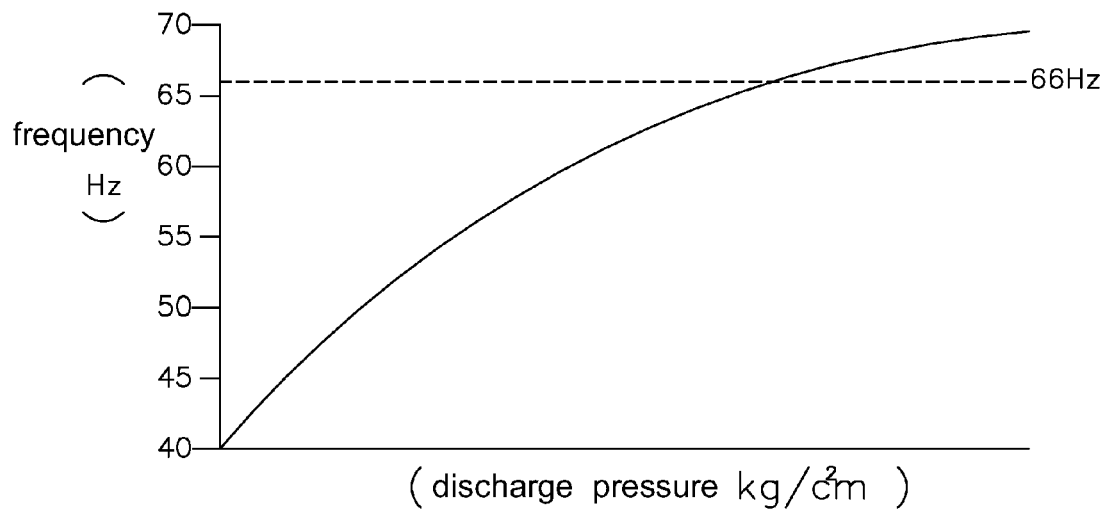
FIG. 23 is a diagram showing the relationship between the oscillating frequency and the discharge pressure according to the above preferred embodiment of the present invention.
Figure 24:
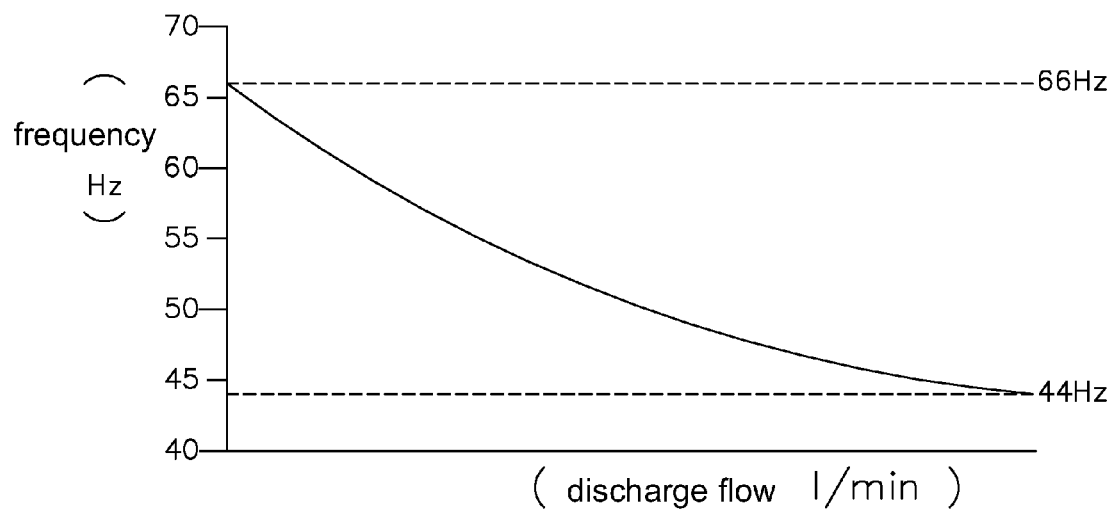
FIG. 24 is a diagram showing the relationship between the oscillating frequency and the discharge flow according to the above preferred embodiment of the present invention.

Referring to FIGS. 23 and 24, the higher the oscillating frequency of the oscillator circuit 43 of the frequency converter circuit 40 of the present invention is, the higher the speed of the switching between the N-phase and the S-phase of the electromagnetic device 27. This further causes the reciprocated swinging of the swing arms 25 to have a higher speed, a higher frequency, and a smaller amplitude; shown on W1 in FIG. 22. As the swing arms 25 reciprocates with a higher speed and frequency, the frequency of the electromagnetic pump 20 correspondingly increases rapidly to increase the suction pressure and the discharge pressure (positive pressure), and as the swing arms 25 reciprocate with a smaller amplitude, the suction flow and the discharge flow of the electromagnetic pump 20 decrease correspondingly. Accordingly, when the oscillating frequency of the oscillator circuit 43 is adjusted to a mid-level frequency (such as 55 Hz), the reciprocated swinging of the swingarms 25 has a medium speed, a medium frequency, and a medium amplitude; shown in W2 on FIG. 11. At this time, the discharge pressure and the discharge flow of the electromagnetic pump 20 are medium.

In view of above, it is appreciated that the electromagnetic pump 20 could have a lower discharge pressure and a higher discharge flow by means of adjusting the oscillating frequency of the oscillator circuit 43 to a lower frequency, and the electromagnetic pump 20 could have a higher discharge pressure and a lower discharge flow by means of adjusting the oscillating frequency of the oscillator circuit 43 to a higher frequency. Accordingly, when the above features are utilized in the nose cleaner, the electromagnetic pump 20 is able to be adjusted to a low frequency to provide for a low discharge pressure and high discharge flow if the patient's nasal cavity is damaged. In other words, the fluid pressure of the fluid injected from the nose-washing tool 5 is low enough to avoid hurting the nasal cavity and the fluid flow of the fluid is large enough to clean the nasal cavity well. For the patients that require a more thorough cleaning in the nasal cavity, the electromagnetic pump 20 is able to be adjusted to a medium frequency to provide for a medium discharge pressure and medium discharge flow or to a high frequency to provide for a high discharge pressure and low discharge flow.

Figure 25A:
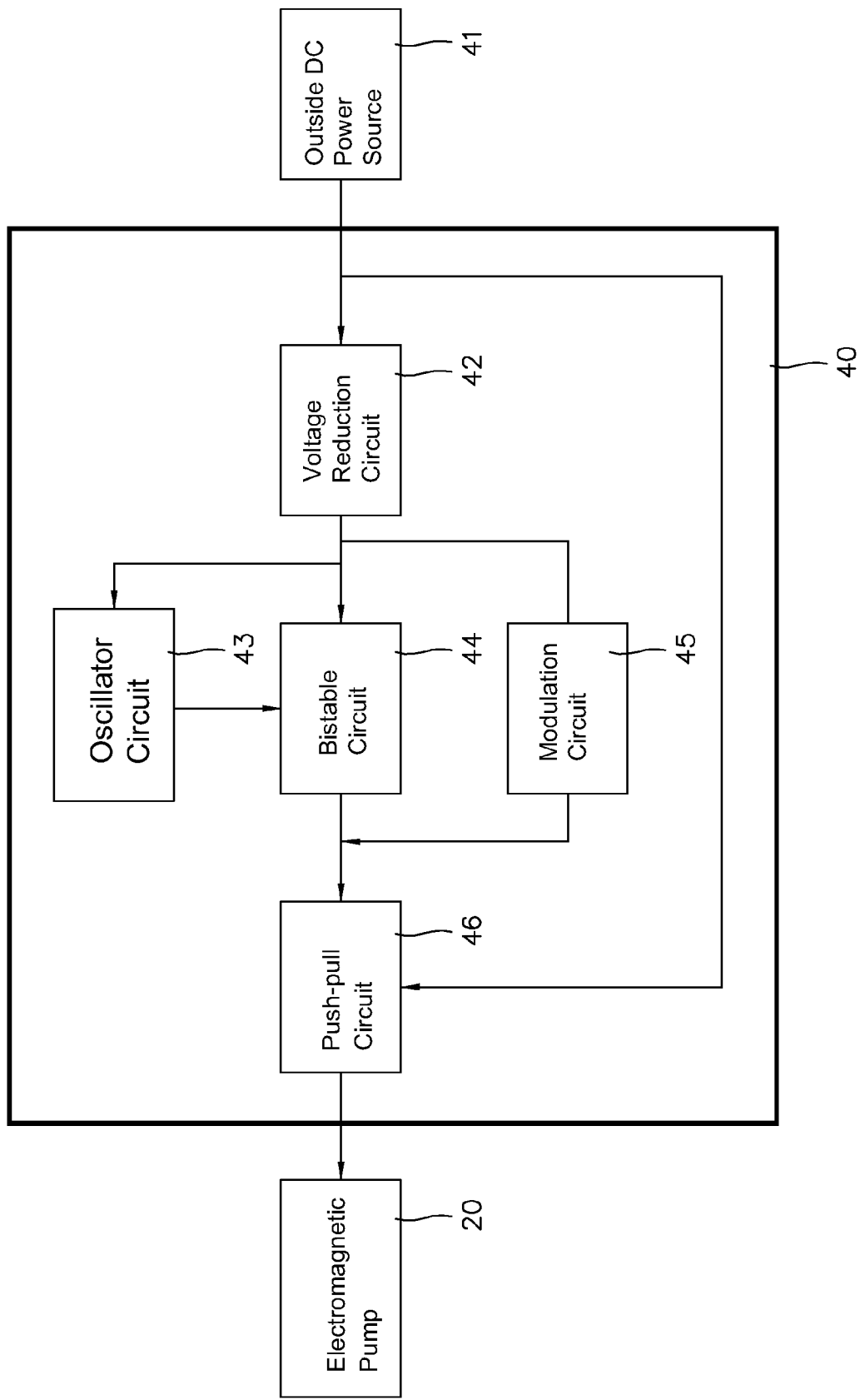
FIG. 25A is a block flow chart of the frequency converter circuit according to a second embodiment of the present invention.
Figure 25B:
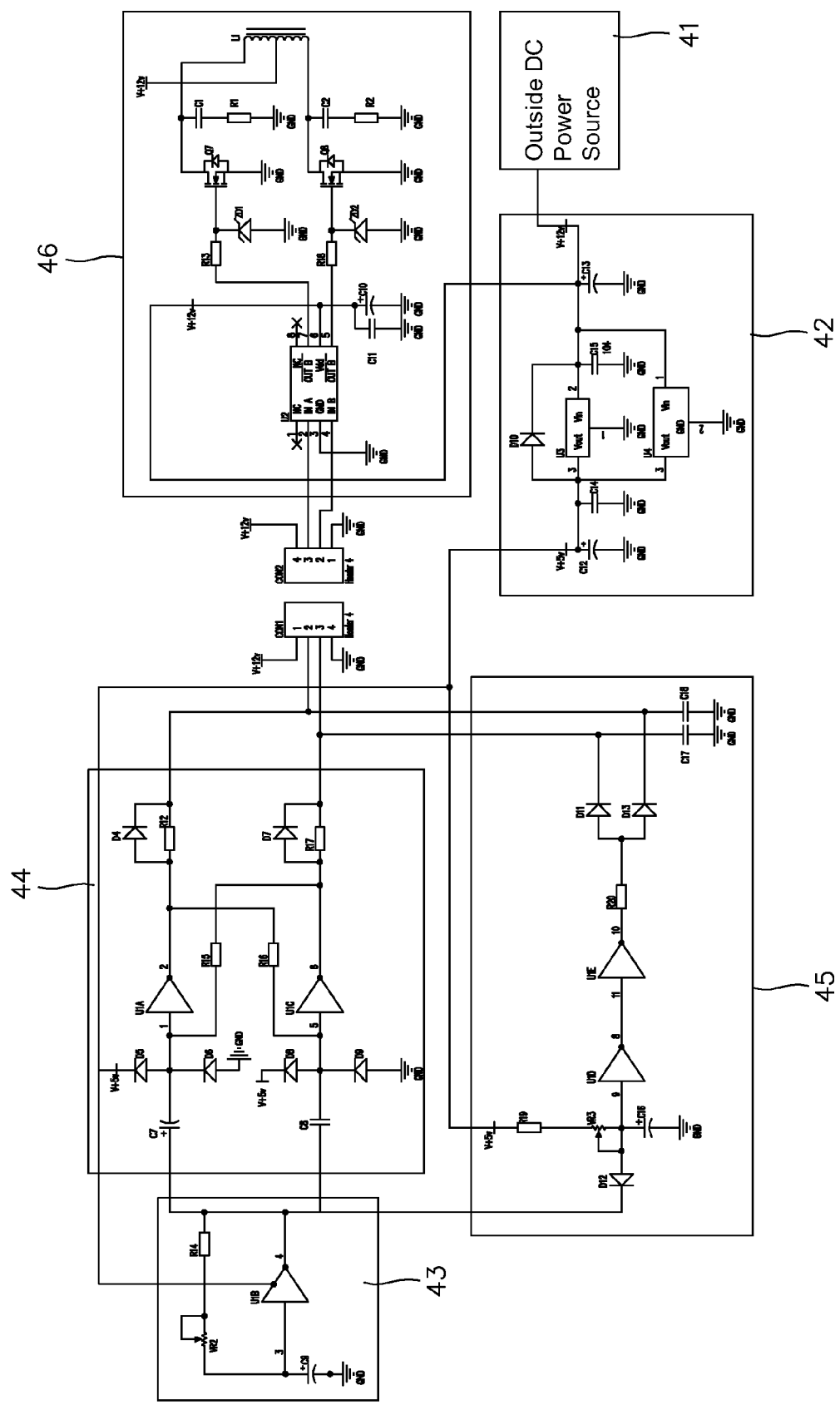
FIG. 25B is a circuit diagram of the circuit of FIG. 25A.

Referring to FIGS. 25A and 25B, a frequency converter circuit 40 of a nose cleaner according to a second preferred embodiment of the present invention is illustrated, which further comprises a modulation circuit 45 which generates a single-phase oscillating signal. The N-phase stimulus signal and the S-phase stimulus signal generated in the bi-stable circuit 44 are mixed with the single-phase oscillating signal respectively to enhance the N-phase stimulus signal while balancing the S-phase stimulus signal or to enhance the S-phase stimulus signal while balancing the N-phase stimulus signal respectively. That enhances the magnetic field strength of the N-phase of the electromagnetic device 27 while balancing the magnetic field strength of the S-phase of the electromagnetic device 27 or enhances the magnetic field strength of the S-phase of the electromagnetic device while balancing the magnetic field strength of the N-phase of the electromagnetic device 27 respectively.

Figure 26:
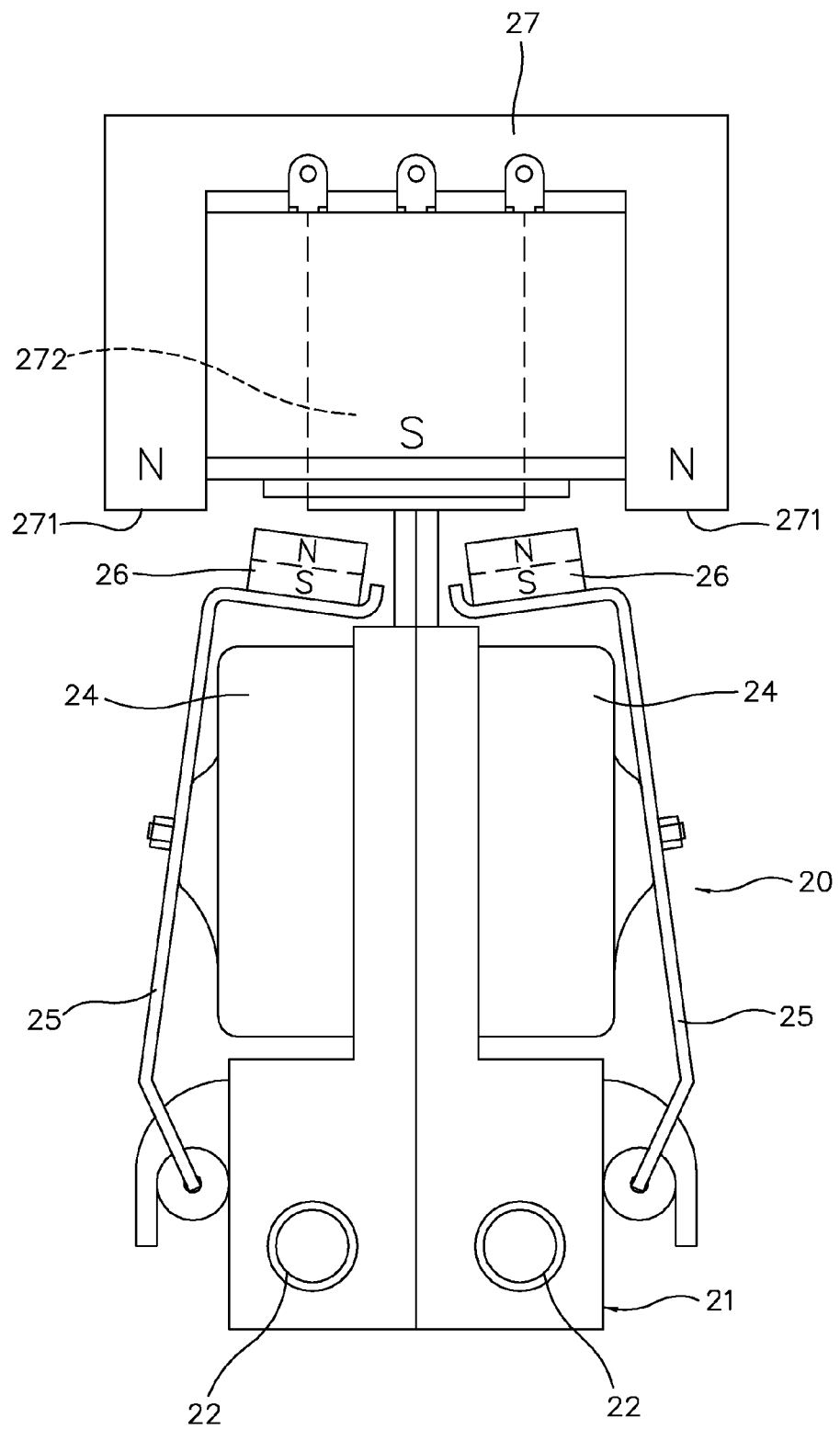
FIG. 26 is a schematic diagram showing the change of the inward swinging of the swing arms after the modulation circuit of the frequency converter circuit is activated according to the above preferred embodiment of the present invention.
Figure 27:
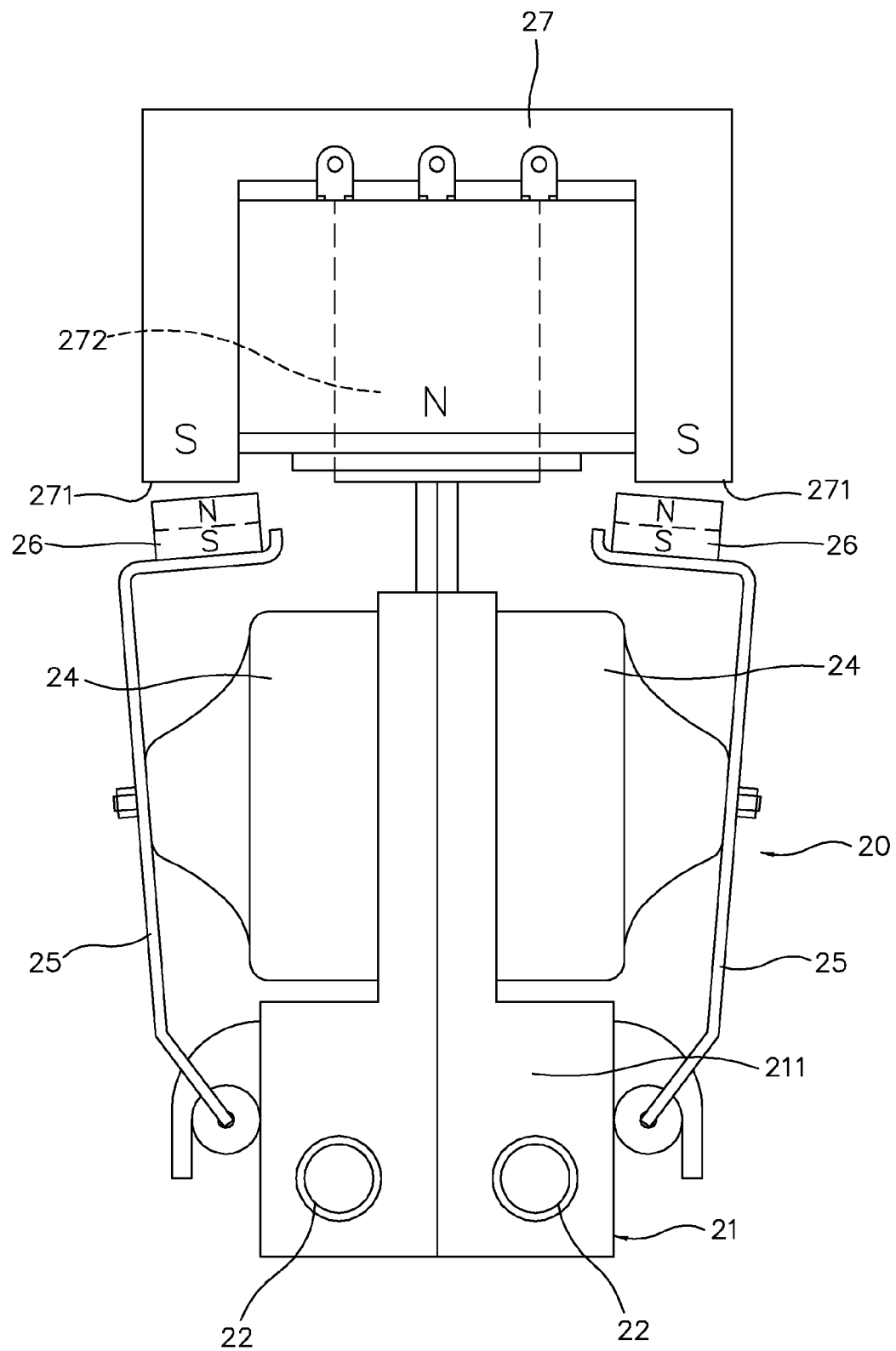
FIG. 27 is a schematic diagram showing the change of the outward swinging of the swing arms after the modulation circuit of the frequency converter circuit is activated according to the above preferred embodiment of the present invention.

The modulation circuit 45 according to the second preferred embodiment is arranged to enhance the magnetic field strength of the S-phase of the electromagnetic device 27 while balancing the magnetic field strength of the N-phase of the electromagnetic device 27. Referring to FIG. 26, when the modulation circuit 45 is activated, the two side magnetic members 271 of the electromagnetic device 27 are switched to the N-phase and the middle magnetic member 272 of the electromagnetic device 27 is switched to the S-phase. As the magnetic members 26 are set to have the outside surfaces of N-phase and the inside surfaces of S-phase, the magnetic members 26 are greatly attracted by the S-phase middle magnetic member 272 of the electromagnetic device 27, which causes the swing arms 25 to swing towards the middle with a higher speed and a greater force. Accordingly, the electromagnetic pump 20 has a higher discharge pressure and a higher discharge flow. Referring to FIG. 27, the middle magnetic member 272 of the electromagnetic device 27 is switched to the N-phase and the two side magnetic members 271 of the electromagnetic device 27 are switched to the S-phase. Due to the mixing of the modulation circuit 45, the N-phase stimulus signal is weakened and causes the N-phase middle magnetic member 272 of the electromagnetic device 27 to have a less powerful magnetic field strength to repulse the magnetic members 26. That causes the swing arms 25 to swing outwardly with a decreased speed and a decreased force. Accordingly, the suction pressure and the suction flow of the electromagnetic pump 20 are decreased. Thereby, when the modulation circuit 45 is activated, the swing arms 25 swings towards the middle with a higher speed and a greater force consistently, while swinging outwards with a lower speed and a smaller force consistently. In the other words, the modulation circuit 45 is arranged to enhance the discharge pressure of the electromagnetic pump 20, of which the nose cleaner could provide a more thorough cleaning.

Figure 32:
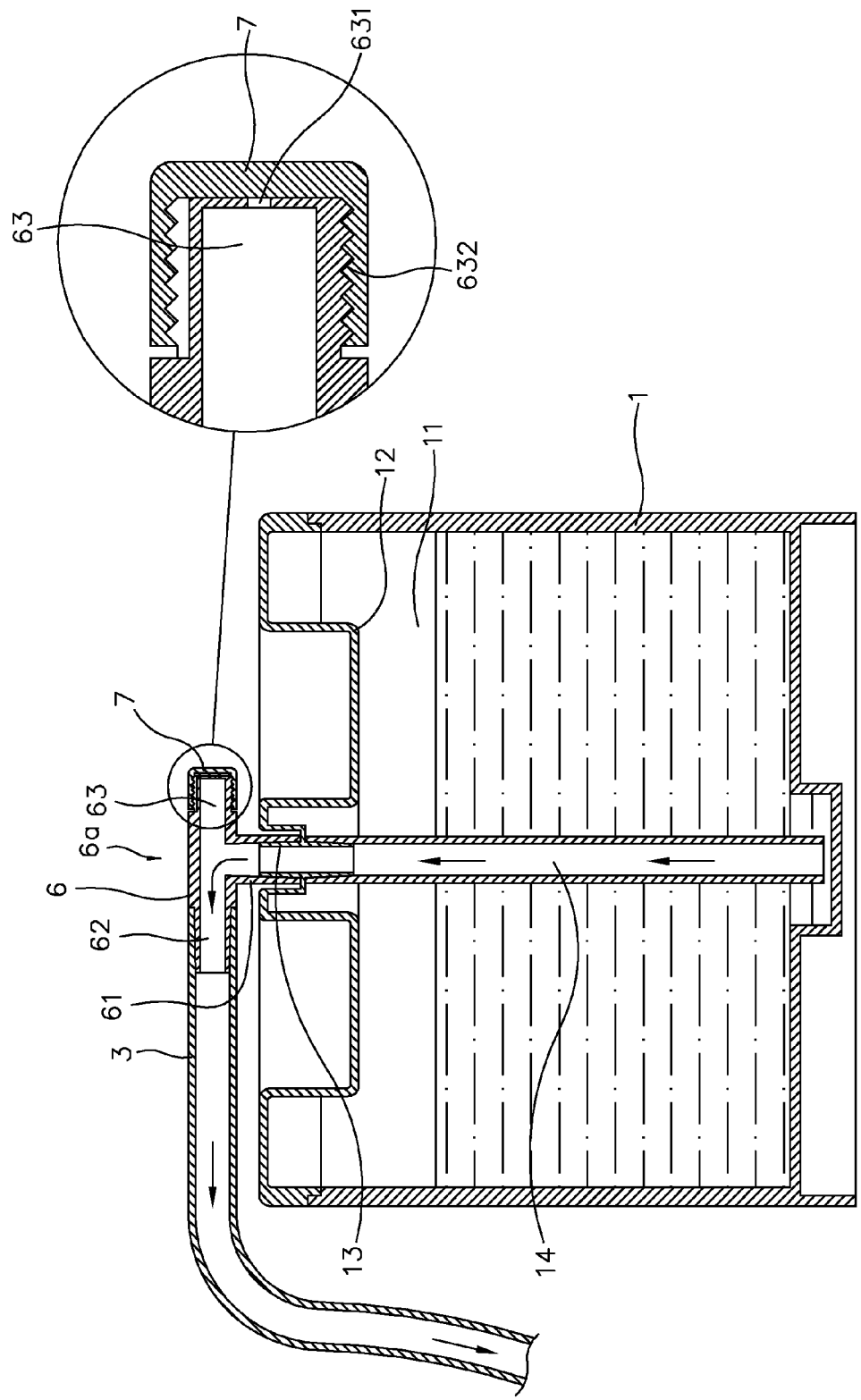
FIG. 32 is a section view illustrating the drawing of the cleaning solution in the container according to the above mentioned preferred embodiment of the present invention.
Figure 33:
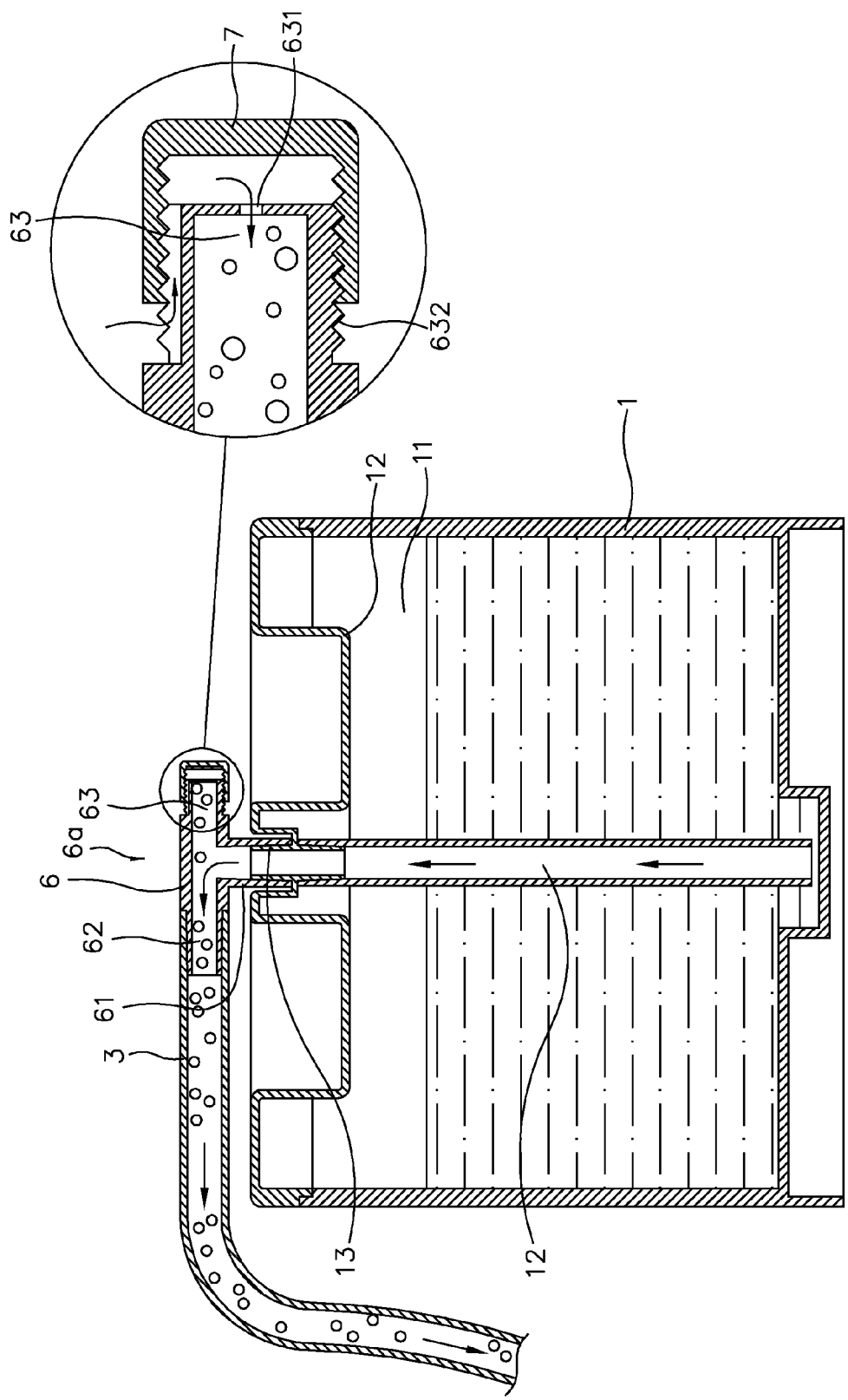
FIG. 33 is a sectional view illustrating the structure of the bubble generating valve in closed condition according to the above preferred embodiment of the present invention.
Figure 34:
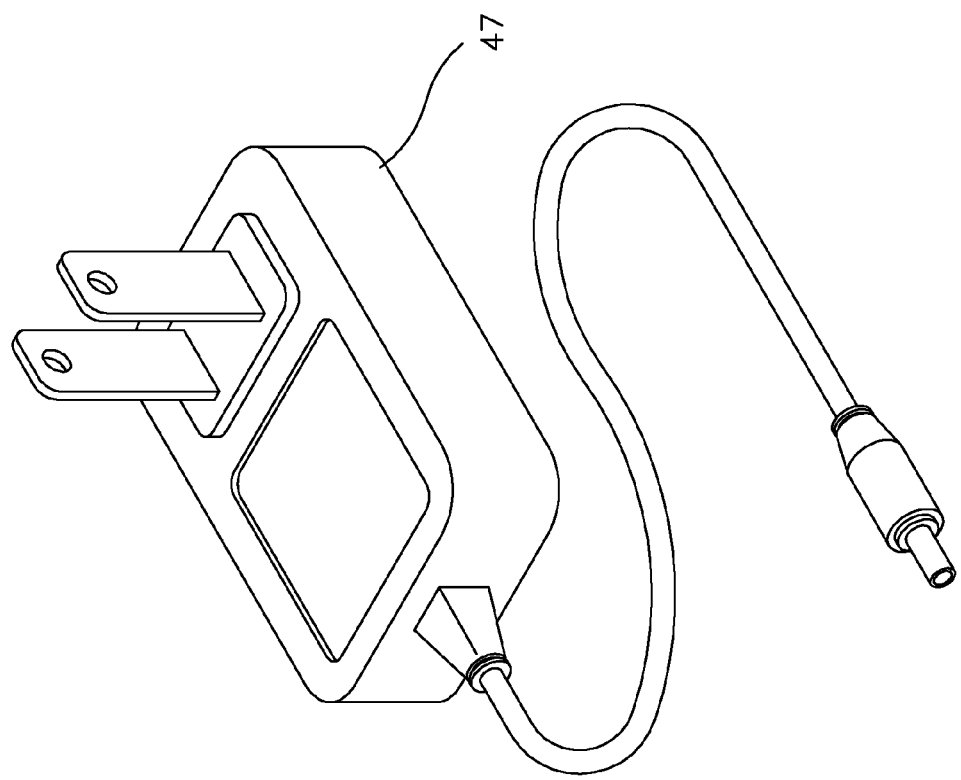
FIG. 34 is a schematic diagram of a transformer rectifier unit.
Figure 35:
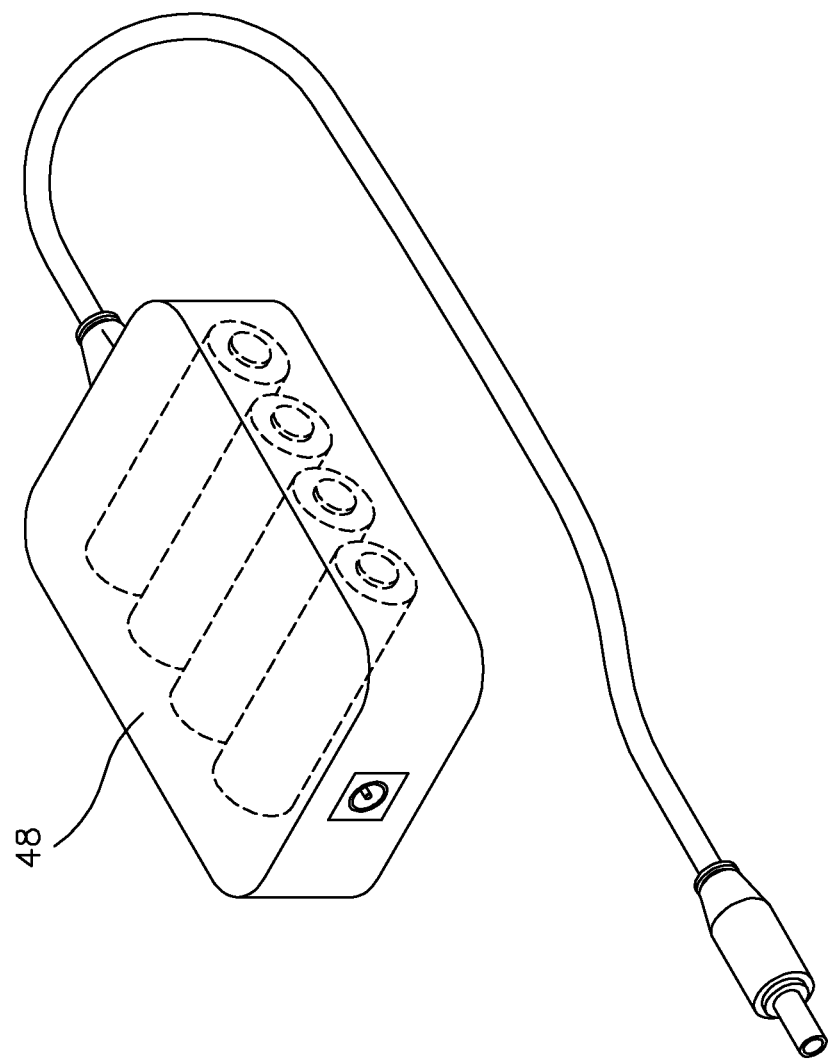
FIG. 35 is a schematic diagram of the battery.
Figure 36:
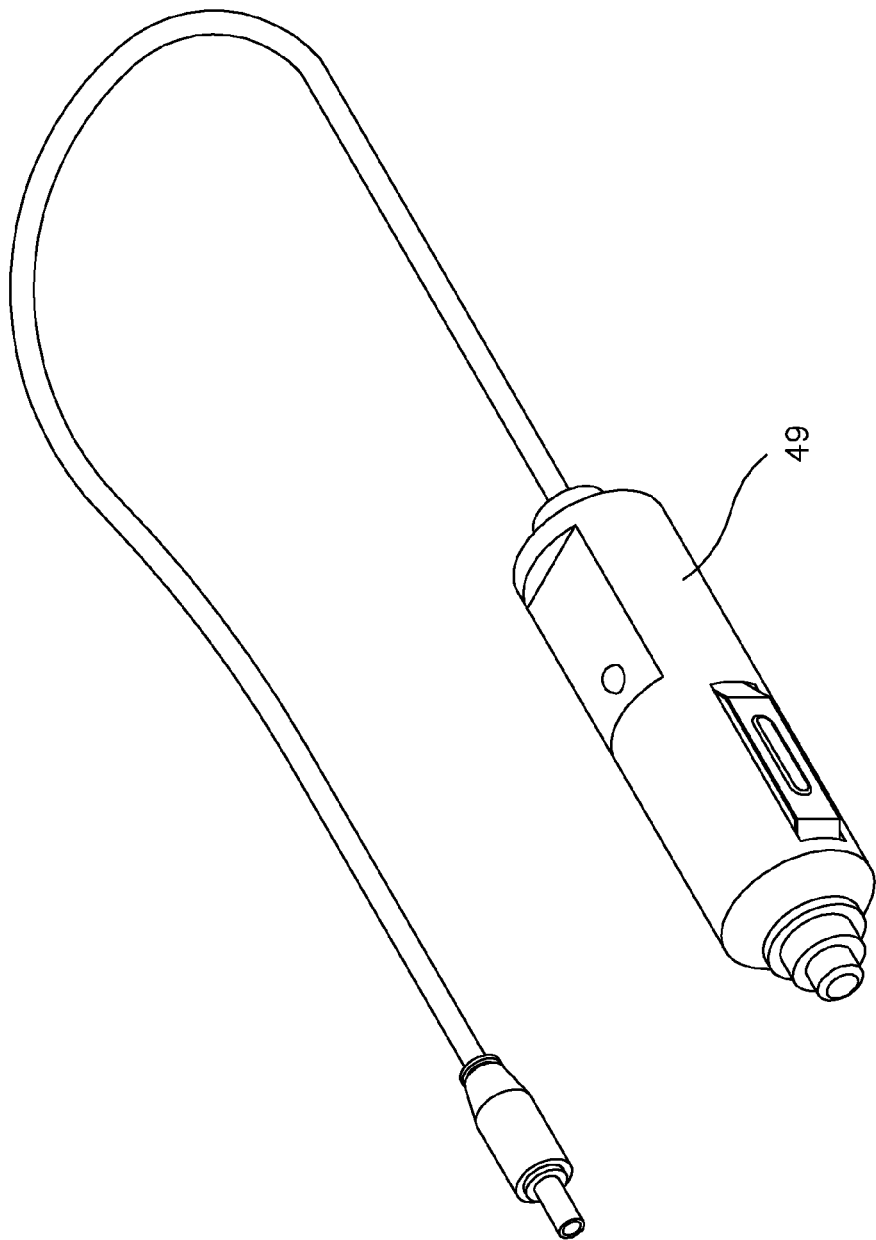
FIG. 36 is a schematic diagram of the electric wire particularly used for the in-car cigarette lighter.

Referring to FIGS. 32 to 33, at least one bubble generating valve 6a is arranged in the fluid path between the container 1 and the nose-washing tool 4. The bubble generating valve 6a comprises a T-shaped three-way connecter 6 and a cap 7. The connector 6 comprises a first tube 61 extended vertically, and a second tube 62 and third tube 63 extended horizontally. The first tube 61 is communicated with the connecting member 13 of the container 1. The second tube 62 is communicated with the soft channel 3 to allow the soft channel 3 to draw the cleaning solution into the container 1 through the connecter 6 and the suction member 14. The third tube 63 has a threaded portion 632 for screwing with the cap 7 so as to control the gas-flow rate of an air inletting opening 631 thereof as well as the opening or closing of this inletting opening 631 so that when the electromagnetic pump 20 draws the cleaning solution into the container 1 the outside air is drawn and sucked in through the air inletting opening 631 to mix with the flowing cleaning solution due to the negative pressure effect thereof and thus the cleaning solution discharged from the nose-washing tool 4 which contains a plurality of air bubbles. As the discharged fluid contains a plurality of bubbles, the bubbles can generally come into contact with the nasal mucosa, so that when the bubbles in the discharged fluid break, oscillating force is generated and applied to the nasal mucosa to massage the mucocilia of the nasal mucosa and clean the dirt in the nasal cavity as well, thereby the cilia on the nasal mucosa can recover their regular movement without the need of using strong pressurized fluid.

Figure 28:
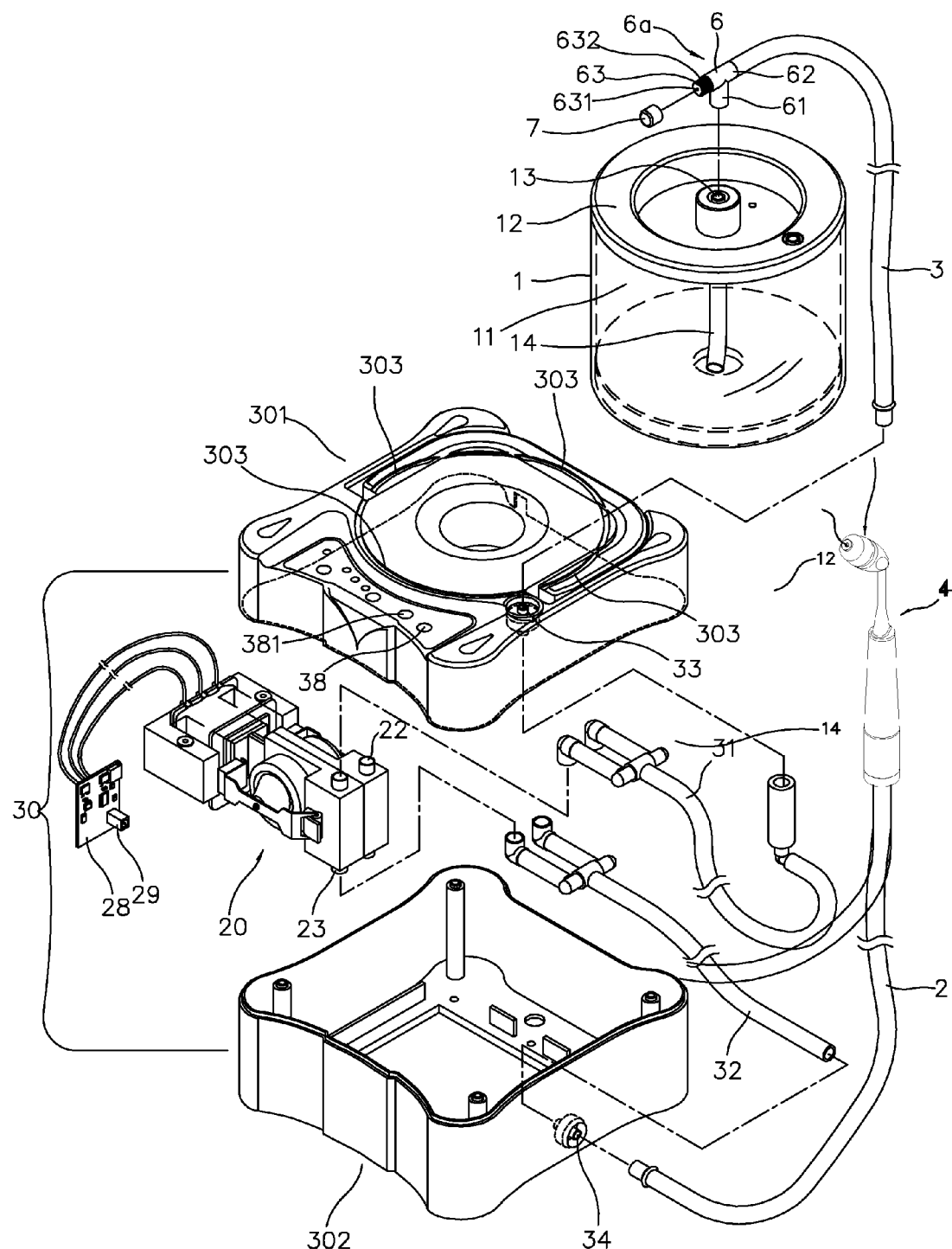
FIG. 28 is a schematic diagram of the electromagnetic pump received in a body according to the above preferred embodiment of the present invention.
Figure 29:
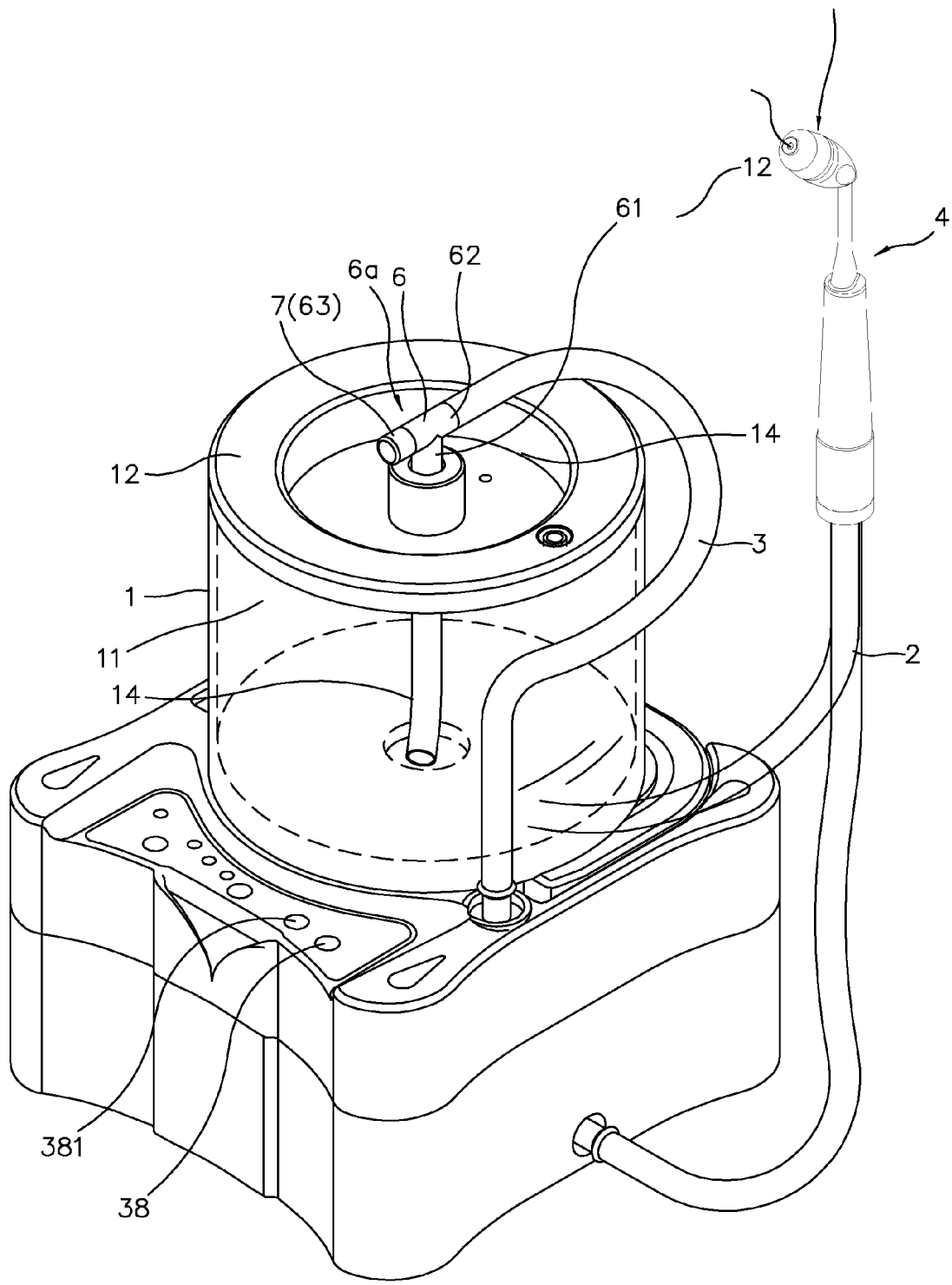
FIG. 29 is an assemble view of the electromagnetic pump of FIG. 28.
Figure 30:
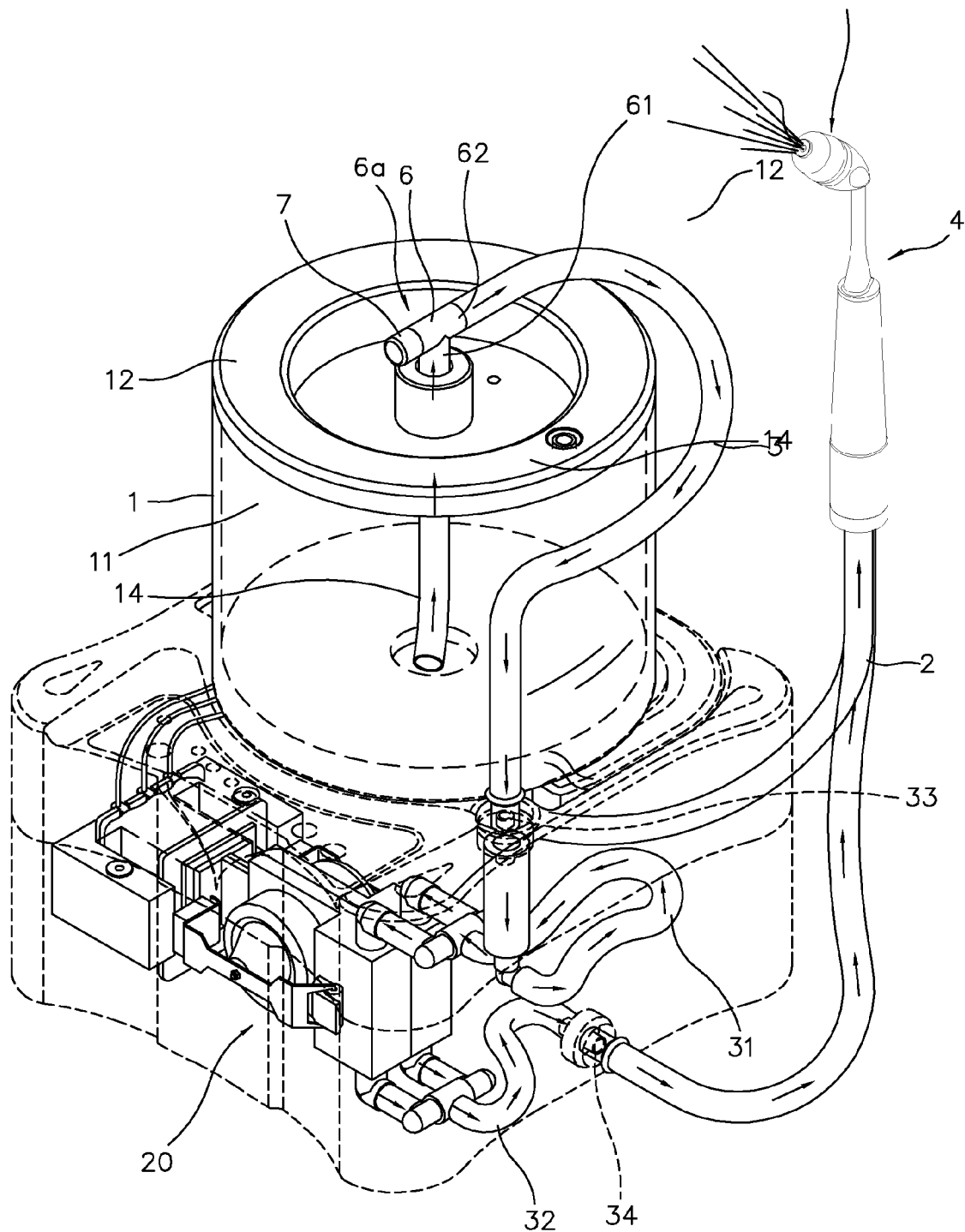
FIG. 30 is a schematic diagram illustrating the flowing direction of the fluid in FIG. 29.

Referring to FIGS. 28 to 30, according to a preferred embodiment of the present invention, the electromagnetic pump 20 and the circuit board 28 are embodied to be contained in a body 30, which has a upper cover 301 and a lower base 302 connected to each other; wherein the upper cover 301 has a ring groove member 303 disposed on the upper surface thereof for being inserted by the bottom edge of the container 1 to support the container 1 onto the upper cover 301. The upper cover 301 further has a negative pressure joint 33 to communicate the inside with the outside, and the lower base 302 has a positive pressure joint 34 to communicate the inside with the outside. The inlet tube 22 of the electromagnetic pump 20 is communicated with the inner end of the negative pressure joint 33 through a negative pressure channel 31. The container 1 is communicated with the outer end of the negative pressure joint 33 through a negative tube 3. The outlet tube 23 of the electromagnetic pump 20 is communicated with the inner end of the positive pressure joint 34 through a positive pressure channel 32. The nose-washing tool 4 is communicated with the outer end of the positive pressure joint 34 through a positive tube 2. Thereby, when the electromagnetic pump 20 is turned on, the cleaning solution in the container 1 is drawn into the electromagnetic pump 20 through the tube 3 and then injected out from the nose-washing tool 4 through tube 2.

Figure 31:
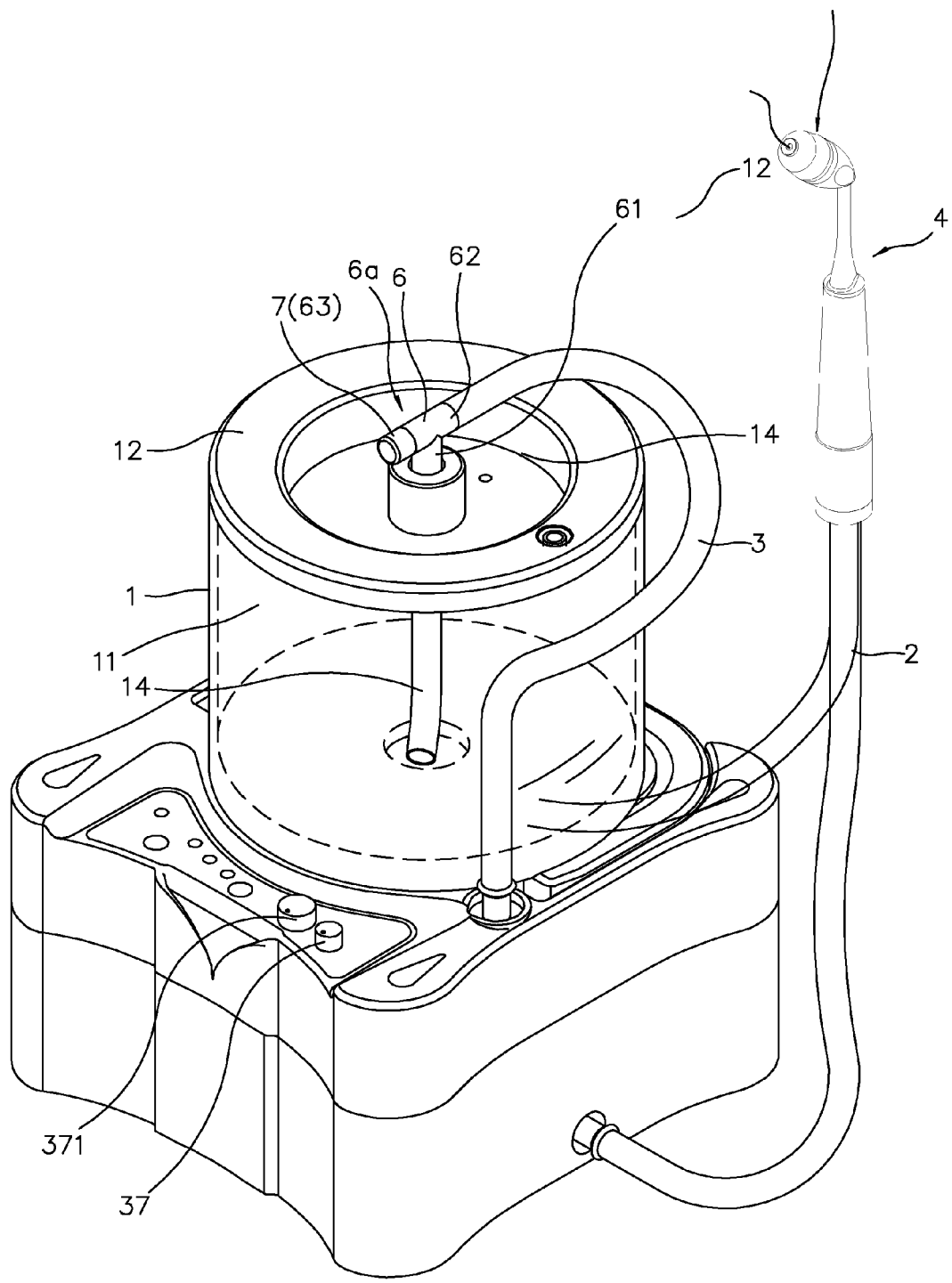
FIG. 31 is a schematic diagram illustrating the connection between the frequency converter circuit and the button of the body according to the above mentioned preferred embodiment of the present invention.

Referring to FIGS. 29 and 31, the oscillation circuit 43 is connected to a first button 37 or a first keypad 38 of the body 30, as shown in FIG. 29. The first button 37 or the first keypad 38 is arranged to activate the oscillation circuit 43 and to adjust the oscillating frequency. In another embodiment, the modulation circuit 45 is connected to a second button 371 or a second keypad 381 of the body 30, as shown in FIG. 31. The second button 371 or the second keypad 381 is arranged to activate the modulation circuit 45 to generate a single-phase oscillating signal and to adjust the single-phase oscillating signal.

Referring to FIGS. 11, 12 and 34 to 36, the external DC power source 41 of the embodiment includes a transformer rectifier unit 47, a battery 48, or an in-car cigarette lighter with 12V DC power source. The circuit board 28 further has a DC socket 29 for connecting to a transformer rectifier unit 47, a battery 48, or an in-car cigarette lighter 49. Hence, it is very convenient for the users to use the present invention of the nose cleaner at home, in the car, or on the subways by connecting the nose cleaner to a suitable power source.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A DC-AC frequency converter-type nose cleaner, comprising:

a container storing a cleaning solution;

an electromagnetic pump which comprises an electromagnetic device, a pump housing, two stretchable and elastic bladders provided at outer surfaces of said pump housing respectively, two swing arms, and two magnetic members, wherein said electromagnetic device has two side magnetic poles and a middle magnetic pole, wherein first ends of said swing arms are disposed on two outer sides of said pump housing respectively, wherein said magnetic members are provided at second ends of said swing arms with a distance from said electromagnetic device, wherein said pump housing is divided into a first chamber and a second chamber, wherein said first chamber has an inlet connector communicated with said container through a negative pressure channel, wherein said second chamber has an outlet connector, wherein said swing arms swing reciprocatingly for drawing said cleaning solution into said first and second chambers from said inlet connecter and discharging said cleaning solution from said outlet connecter;

a nose-washing tool having a fluid inlet end communicated with said outlet connector through a positive pressure channel, and a fluid outlet end, wherein said nose-washing tool comprises a spray nozzle provided at said fluid outlet end, wherein when said electromagnetic pump is activated, said negative pressure channel draws said cleaning solution in said container and supplies said cleaning solution to said nose-washing tool for discharging said cleaning solution from said spray nozzle;

a frequency converter circuit which comprises an oscillator circuit for transforming DC into a single-phase oscillating signal, a bistable circuit and a push-pull circuit, wherein said bistable circuit splits said single-phase oscillating signal into a N-phase stimulus signal and a S-phase stimulus signal, wherein both said N-phase stimulus signal and said S-phase stimulus signal respectively activate magnetism of said two side magnetic poles of said electromagnetic device and magnetism of middle magnetic pole of said electromagnetic device to alternatively switch between a N-phase and a S-phase, wherein said two side magnetic poles and said middle magnetic pole are selectively attracted or repulsed by said two magnetic members respectively to force said swing arms to swing reciprocatingly, wherein said push-pull circuit amplifies and transports said N-phase stimulus signal and said S-phase stimulus signal to said electromagnetic pump to force said swing arms of said electromagnetic pump to swing effectively, wherein said frequency converter circuit is arranged for using said DC to activate said swing arms of said electromagnetic pump to swing reciprocatingly, wherein oscillating frequency of said oscillator circuit is adjusted to change a swing speed, a swing frequency and a swing amplitude of said swing arms of said electromagnetic pump, so as to further change a discharge pressure and a discharge flow of said electromagnetic pump for said nose cleaner.

2. The DC-AC frequency converter-type nose cleaner, as recited in claim 1, wherein said frequency converter circuit further comprises a modulation circuit which generates a single-phase oscillating signal, wherein said N-phase stimulus signal and said S-phase stimulus signal generated in said bistable circuit are mixed with said single-phase oscillating signal respectively to enhance said S-phase stimulus signal while balancing said N-phase stimulus signal, so as to further enhance a magnetic field strength of said S-phase of said electromagnetic device, and to cause said swing arms to swing inwardly with a higher speed and a bigger force and to swing outwardly with a lower speed and a smaller force, in order to increase said discharge pressure of said electromagnetic pump.

3. The DC-AC frequency converter-type nose cleaner, as recited in claim 1, wherein said frequency converter circuit further comprises a voltage reduction circuit arranged for voltage stabilizing, wherein said voltage reduction circuit transforms DC inputted into said frequency converter circuit into DC with a lower voltage, which is supplied to each of said oscillator circuit, said bistable circuit and said push-pull circuit as a working current.

4. The DC-AC frequency converter-type nose cleaner, as recited in claim 1, wherein said DC is supplied by a transformer rectifier unit.

5. The DC-AC frequency converter-type nose cleaner, as recited in claim 1, wherein said DC is supplied by a battery.

6. The DC-AC frequency converter-type nose cleaner, as recited in claim 1, wherein said DC is supplied by an in-car cigarette lighter which is connected to said nose cleaner by a wire.

7. The DC-AC frequency converter-type nose cleaner, as recited in claim 1, wherein said oscillator circuit is a Schmitt oscillator circuit.

8. The DC-AC frequency converter-type nose cleaner, as recited in claim 1, wherein said container has an upper opening enabling an upper cover to cover thereon, wherein said upper cover has a connecting member provided thereon, wherein a suction member is connected to a bottom of said connecting member for drawing said cleaning solution in said container upwardly, wherein said connecting member is communicated with said inlet connecter of said electromagnetic pump through said negative pressure channel, wherein a bubble generating valve, which is communicated with said negative pressure channel, comprises a three-way connector and a cap, wherein said three-way connector comprises a vertical first tube communicated with said connecting member of said container, a horizontal second tube communicated with said negative pressure channel and a horizontal third tube having an air inletting opening provided at one end for communicating with outside, wherein said third tube is screwed with said cap to control a gas-flow rate of said bubble generating valve to selectively control a gas-flow rate of said air inletting opening thereof or to open or close said air inletting opening, wherein said air inletting opening is opened for drawing and sucking outside air to mix with said cleaning solution due to said negative pressure effect thereof so as to ensure said cleaning solution being discharged from said spray nozzle that substantially contains a large amount of air bubbles.

9. The DC-AC frequency converter-type nose cleaner, as recited in claim 1, wherein said magnetic member has a N-phase outside surface and a S-phase inside surface.

10. The DC-AC frequency converter-type nose cleaner, as recited in claim 1, wherein said first chamber and said second chamber are orientated in up and down positions.

11. The DC-AC frequency converter-type nose cleaner, as recited in claim 1, wherein said electromagnetic pump is contained in a body which has at least one negative pressure joint and at least one positive pressure joint, wherein said negative pressure joint has an end communicated with said container through a negative tube and another end communicated with said inlet connecter of said electromagnetic pump through said negative pressure channel, wherein said positive pressure joint has an end communicated with said nose-washing tool through a positive tube and another end communicated with said outlet connecter of said electromagnetic pump through said positive pressure channel.

12. The DC-AC frequency converter-type nose cleaner, as recited in claim 2, wherein said electromagnetic pump is contained in a body which has at least one negative pressure joint and at least one positive pressure joint, wherein said negative pressure joint has an end communicated with said container through a negative tube and another end communicated with said inlet connecter of said electromagnetic pump through a negative pressure channel, wherein said positive pressure joint has an end communicated with said nose-washing tool through a positive tube and another end communicated with said outlet connecter of said electromagnetic pump through a positive pressure channel.

13. The DC-AC frequency converter-type nose cleaner, as recited in claim 1, wherein said electromagnetic pump and said frequency circuit are contained in a body which has an upper cover and a lower base connected with each other, wherein said upper cover has a ring groove member disposed on an upper surface thereof for being inserted by a bottom edge of said container to support said container onto said upper cover.

14. The DC-AC frequency converter-type nose cleaner, as recited in claim 11, wherein said oscillation circuit is connected to a button of said body to activate said oscillation circuit and to adjust said oscillating frequency thereof.

15. The DC-AC frequency converter-type nose cleaner, as recited in claim 11, wherein said oscillation circuit is connected to a keypad of said body to activate said oscillation circuit and to adjust said oscillating frequency thereof.

16. The DC-AC frequency converter-type nose cleaner, as recited in claim 12, wherein said modulation circuit is connected to a button of said body which is arranged to activate said modulation circuit to generate a single-phase oscillating signal and to adjust said single-phase oscillating signal.

17. The DC-AC frequency converter-type nose cleaner, as recited in claim 12, wherein said modulation circuit is connected to a keypad of said body which is arranged to activate said modulation circuit to generate a single-phase oscillating signal and to adjust single-phase oscillating signal.

18. The DC-AC frequency converter-type nose cleaner, as recited in claim 1, wherein said nose-washing tool comprises:
an extension channel with an inner hole inside and a containing house disposed at an end thereof;
a fixing head disposed at said containing house of said extension channel, wherein said fixing head has a head element for closing said containing house, a guiding house formed in said head element and communicated with said containing house, and a fluid outlet hole provided in said head element and communicated with said guiding house;
a handle member disposed on another end of said extension channel, wherein said handle member has a connecting channel therein, wherein said connecting channel has a first end communicated with said inner hole of said extension channel and a second end for providing said cleaning solution; and
a touch sensitive switch and a spring, both of which are disposed in an inner space formed between said containing house of said extension channel and said guiding house of said fixing head, wherein said touch sensitive switch is forced by said spring to close said fluid outlet hole of said fixing head to stop discharging said cleaning solution;
wherein said spray nozzle is disposed on a forward end of said touch sensitive switch, wherein said spray nozzle has a sleeve engaged with said head element of said fixing head and a through-hole for injecting said cleaning solution, wherein said spray nozzle is able to slide along said head element of said fixing head; whereby when said spray nozzle is touched with a nasal cavity, said touch sensitive switch moves a distance to open said fluid outlet hole of said head element to discharge said cleaning solution from said through-hole of said spray nozzle.

19. The DC-AC frequency converter-type nose cleaner, as recited in claim 18, wherein said touch sensitive switch has a shoulder member sliding along said guiding house and a spindle extended downwardly from a center of said shoulder member, wherein said spindle, which has a top, sleeved by said spray nozzle and is drilled through said fluid outlet hole of said head element, is able to move forth and back; wherein said spindle further has a spray hole disposed on a top thereof and a fluid guiding hole radically formed in a portion thereof towards said shoulder, wherein said spray hole is communicated with said through-hole of said spray nozzle, wherein said fluid guiding hole is communicated with said spray hole, wherein said shoulder member is communicated with said guiding house and a hole of said containing house, wherein a center shaft is sleeved in and extended along said spring, wherein said spring has an end supported on a bottom of said containing house and another end supported on said shoulder member, wherein said shoulder member is supported onto an inner top surface of said guiding house due to a force of said spring, wherein said hole is closed by said inner top surface of said guiding house and said fluid guiding hole is closed by said inner surface of said fluid outlet hole to stop discharging said cleaning solution, wherein when said spray nozzle is arranged for touching with said nasal cavity, said touch sensitive switch moves a distance to make said shoulder member leaving said inner top surface of said guiding house, whereby said cleaning solution flows through said hole and flows into said spray hole of said spindle through said fluid guiding hole, and thus said cleaning solution is finally injected off from said through-hole of said spray nozzle.

20. The DC-AC frequency converter-type nose cleaner, as recited in claim 18, wherein said handle member has a platform on a top end thereof, an insert channel disposed on a bottom of said the platform and extended inside said handle member; wherein said platform has two arcuate insert grooves and two arcuate block grooves, which are respectively and symmetrically arranged on said platform and centered on said insert channel, wherein said arcuate insert grooves are respectively communicated with said arcuate block grooves, wherein each of said arcuate block grooves has a smaller groove width than that of said arcuate insert groove and has an arcuate resist groove disposed on a bottom thereof, wherein each of said arcuate resist grooves has the same groove width as that of said arcuate insert groove; wherein said extension channel has a fixing base mated with said platform and a receiving channel disposed on a bottom of said the fixing base and mated with said insert channel, wherein said fixing base has two arcuate plates and two arcuate blocks respectively disposed on bottoms of said arcuate plates and radically extruded therefrom, wherein said two arcuate plates and said two arcuate blocks are respectively inserted into said arcuate insert grooves and rotate towards said arcuate block grooves, wherein said arcuate blocks are respectively located inside said arcuate resist grooves on bottoms of said arcuate block grooves.

* * * * *